(12) United States Patent
Takegami et al.

(10) Patent No.: US 10,947,472 B2
(45) Date of Patent: Mar. 16, 2021

(54) LUBRICANT BASE OIL FOR POWER TRANSMISSION

(71) Applicant: NEW JAPAN CHEMICAL CO., LTD., Kyoto (JP)

(72) Inventors: Akinobu Takegami, Kyoto (JP); Shinya Tsujimoto, Kyoto (JP); Yasuyuki Kawahara, Kyoto (JP); Jun Itsuki, Kyoto (JP)

(73) Assignee: NEW JAPAN CHEMICAL CO., LTD., Kyoto (JP)

( * ) Notice: Subject to any disclaimer, the term of this patent is extended or adjusted under 35 U.S.C. 154(b) by 0 days.

(21) Appl. No.: 16/314,722

(22) PCT Filed: Jul. 5, 2017

(86) PCT No.: PCT/JP2017/024586
§ 371 (c)(1),
(2) Date: Jan. 2, 2019

(87) PCT Pub. No.: WO2018/008667
PCT Pub. Date: Jan. 11, 2018

(65) Prior Publication Data
US 2019/0249103 A1  Aug. 15, 2019

(30) Foreign Application Priority Data

Jul. 7, 2016  (JP) .................................. 2016-134982

(51) Int. Cl.
*C07C 69/75* (2006.01)
*A01F 12/00* (2006.01)
(Continued)

(52) U.S. Cl.
CPC ........... *C10M 129/72* (2013.01); *C07C 69/75* (2013.01); *C07C 69/753* (2013.01);
(Continued)

(58) Field of Classification Search
CPC ............ C10M 129/72; C10M 105/36; C10M 169/04; C10M 2207/2825;
(Continued)

(56) References Cited

U.S. PATENT DOCUMENTS

| 5,126,065 A | 6/1992 | Tsubouchi et al. |
| 2005/0038283 A1* | 2/2005 | Kawahara ............... C07C 69/75 560/76 |
| 2010/0237274 A1 | 9/2010 | Ota et al. |

FOREIGN PATENT DOCUMENTS

| JP | 59-191797 A | 10/1984 |
| JP | 3-95295 A | 4/1991 |

(Continued)

OTHER PUBLICATIONS

International Search Report dated Aug. 8, 2017, issued in counterpart International Application No. PCT/JP2017/024586, with English Translation. (4 pages).

*Primary Examiner* — Prem C Singh
*Assistant Examiner* — Francis C Campanell
(74) *Attorney, Agent, or Firm* — Westerman, Hattori, Daniels & Adrian, LLP

(57) ABSTRACT

An object of the present invention is to provide a lubricant base oil for power transmission (in particular, a lubricant base oil for traction drives) having a high traction coefficient and a high flash point. The present invention relates to a lubricant base oil for power transmission comprising an alicyclic dicarboxylic acid diester compound represented by general formula (1):

(Continued)

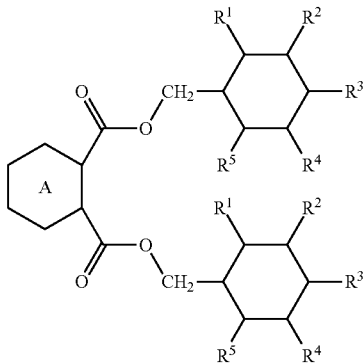

(1)

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; and ring A is

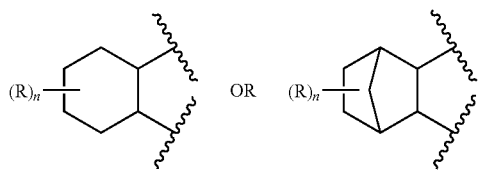

wherein R represents $C_{1-3}$ alkyl, and n represents 0, 1, or 2; when n represents 2, R may be the same or different.

15 Claims, 27 Drawing Sheets

(51) Int. Cl.
C10M 129/72 (2006.01)
C10M 105/36 (2006.01)
C07C 69/753 (2006.01)
C10M 169/04 (2006.01)
C10N 30/02 (2006.01)
C10N 30/06 (2006.01)
C10N 30/08 (2006.01)
C10N 40/04 (2006.01)
C10N 40/08 (2006.01)

(52) U.S. Cl.
CPC ........ *C10M 105/36* (2013.01); *C10M 169/04* (2013.01); *C07C 2601/14* (2017.05); *C07C 2602/42* (2017.05); *C10M 2203/003* (2013.01); *C10M 2207/282* (2013.01); *C10M 2207/2825* (2013.01); *C10N 2030/02* (2013.01); *C10N 2030/06* (2013.01); *C10N 2030/08* (2013.01); *C10N 2040/04* (2013.01); *C10N 2040/046* (2020.05); *C10N 2040/08* (2013.01)

(58) Field of Classification Search
CPC ....... C10M 2207/282; C10M 2203/003; C07C 69/75; C07C 69/753; C07C 2602/42; C07C 2601/14; C10N 2230/08; C10N 2230/06; C10N 2240/046
USPC .......................................... 508/484; 560/76
See application file for complete search history.

(56) References Cited

FOREIGN PATENT DOCUMENTS

| JP | 2001-89776 A | 4/2001 |
|---|---|---|
| JP | 2008-56800 A | 3/2008 |
| JP | 2011-79794 A | 4/2011 |
| JP | 2014-015525 | * 1/2014 |
| JP | 2016-108543 A | 6/2016 |
| JP | 6274326 B2 | 2/2018 |
| WO | 01/05740 A1 | 1/2001 |
| WO | 2016/093088 A1 | 6/2016 |

* cited by examiner

LUBRICANT BASE OIL FOR POWER TRANSMISSION

TECHNICAL FIELD

The present invention relates to a lubricant base oil for power transmission. Specifically, the present invention relates to a lubricant base oil for traction drives.

BACKGROUND ART

In recent years, the digital information society has progressed, and higher accuracy has been required for printers and copying machines. In particular, for motor sections for which highly accurate paper feeding is required, high rotation accuracy, low vibration, and low noise are required. Gear systems employed as power transmission means for these rotating parts cause a great deal of vibration and noise; thus, traction drives with less vibration and noise are often used.

Moreover, the dissemination of industrial robots has also progressed. Traction drives are also used in their joint portions, for which precise movement is required. In addition, traction drives have been increasingly put into practical use in the field of continuously variable transmissions for industrial machines, aircraft generators, helicopter rotor rotation controls, and the like. Increasing the size of traction drives is currently under consideration for the purpose of increasing the amount of power transmission; however, calorific power also tends to increase along with the increase in the contact area.

Lubricant base oils for traction drives having a high traction coefficient are preferable for higher power transmission performance, and alicyclic hydrocarbon compounds etc. have been proposed. Examples include dicyclohexyl compounds represented by 2-methyl-2,4-dicyclohexylpentane, and dimerized norbornanes (PTL 1 and PTL 2).

However, alicyclic hydrocarbon compounds represented by 2-methyl-2,4-dicyclohexylpentane are highly likely to have a flash point as low as 200° C. or less. They are not always satisfactory in fields in which large traction drives etc. are employed, and in which heat resistance and safety are regarded as important.

CITATION LIST

Patent Literature

PTL 1: JPS47-7664A
PTL 2: JPH03-95295A

SUMMARY OF INVENTION

Technical Problem

An object of the present invention is to provide a lubricant base oil for power transmission (particularly a lubricant base oil for traction drives) that has a high traction coefficient and a high flash point.

Solution to Problem

The present inventors found that a specific alicyclic dicarboxylic acid diester compound had a high traction coefficient and a high flash point. The present invention has been completed upon further consideration based on this finding.

Specifically, the present invention provides lubricant base oils for power transmission (particularly lubricant base oils for traction drives) according to the following items.

[Item 1]
A lubricant base oil for power transmission comprising an alicyclic dicarboxylic acid diester compound represented by general formula (1):

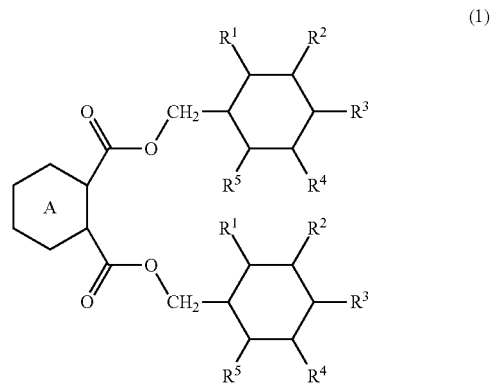

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; and ring A is

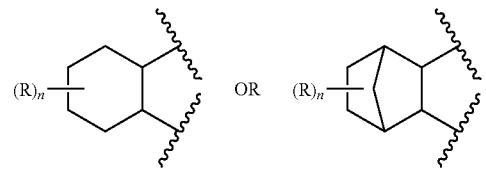

wherein R represents $C_{1-3}$ alkyl, and n represents 0, 1, or 2; when n represents 2, R may be the same or different.

[Item 2]
The lubricant base oil for power transmission according to item 1, wherein $R^1$ and $R^5$ are hydrogen.

[Item 3]
The lubricant base oil for power transmission according to item 1 or 2, wherein $R^1$, $R^2$, and $R^5$ are hydrogen.

[Item 4]
The lubricant base oil for power transmission according to any one of items 1 to 3, wherein n is 0 or 1; and R represents $C_{1-3}$ alkyl (preferably methyl).

[Item 5]
The lubricant base oil for power transmission according to any one of items 1 to 4, wherein ring A is

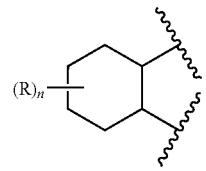

wherein R and n are as defined above.

[Item 6]
The lubricant base oil for power transmission according to any one of items 1 to 4, wherein the content of the alicyclic dicarboxylic acid diester compound represented by general formula (1) in the lubricant base oil for power transmission is 70 wt % or more.

[Item 7]

The lubricant base oil for power transmission according to any one of items 1 to 6, wherein the traction coefficient at 60° C. is 0.095 or more.

[Item 8]

The lubricant base oil for power transmission according to any one of items 1 to 7, wherein the flash point is 210° C. or more.

[Item 9]

The lubricant base oil for power transmission according to any one of items 1 to 8, wherein the pour point is 3° C. or less (preferably 1° C. or less, more preferably −5° C. or less).

[Item 10]

The lubricant base oil for power transmission according to any one of items 1 to 9, wherein the kinetic viscosity at 100° C. is 4 to 25 mm²/s (preferably 5 to 20 mm²/s)

[Item 11]

The lubricant base oil for power transmission according to any one of items 1 to 10, wherein the lubricant base oil for power transmission is a lubricant base oil for traction drives.

[Item 12]

A lubricant oil for power transmission comprising the lubricant base oil for power transmission according to any one of items 1 to 11.

[Item 13]

The lubricant oil for power transmission according to any one of items 1 to 12, further comprising at least one additive selected from the group consisting of antioxidants, metal detergents, ashless dispersants, oiliness agents, antiwear agents, extreme-pressure agents, metal deactivators, rust inhibitors, viscosity index improvers, pour point depressants, antifoaming agents, hydrolysis inhibitors, thickeners, corrosion inhibitors, and hue stabilizers.

[Item 14]

An alicyclic dicarboxylic acid diester compound represented by general formula (1):

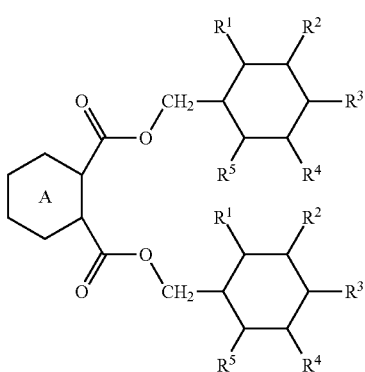

(1)

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; and ring A is

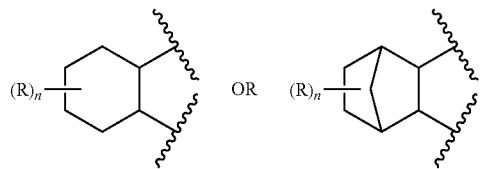

wherein R represents $C_{1-3}$ alkyl, and n represents 0, 1, or 2; when n represents 2, R may be the same or different.

[Item 15]

The alicyclic dicarboxylic acid diester compound according to item 14, wherein ring A is

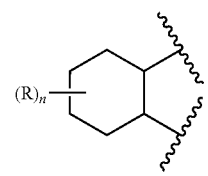

wherein R and n are as defined above.

[Item 16]

The alicyclic dicarboxylic acid diester compound according to any one of item 14 or 15, wherein (a) R is $C_{1-3}$ alkyl (in particular, methyl) and n is 1 or 2; or (b) $R^3$ and/or $R^4$ is linear or branched $C_{1-4}$ alkyl (in particular, methyl).

[Item 17]

The alicyclic dicarboxylic acid diester compound according to any one of items 14 to 16, wherein (a') R is $C_{1-3}$ alkyl (in particular, methyl) and n is 1; or (b') one of $R^3$ and $R^4$ is linear or branched $C_{1-4}$ alkyl (in particular, methyl), while the other is hydrogen, or both of $R^3$ and $R^4$ are linear or branched $C_{1-4}$ alkyl (in particular, methyl), and $R^1$, $R^2$, and $R^5$ are hydrogen.

[Item 18]

The alicyclic dicarboxylic acid diester compound according to any one of items 14 to 17, wherein the acid value is 0.1 mg KOH/g or less, and the hydroxyl value is 2 mg KOH/g or less.

[Item 19]

The alicyclic dicarboxylic acid diester compound according to any one of items 14 to 18, wherein the traction coefficient at 60° C. is 0.095 or more.

[Item 20]

A method for improving the traction coefficient of a lubricant oil for power transmission, comprising incorporating the lubricant base oil for power transmission according to any one of items 1 to 11, or the alicyclic dicarboxylic acid diester compound according to any one of items 14 to 19 in a lubricant oil for power transmission.

[Item 21]

Use of the lubricant base oil for power transmission according to any one of items 1 to 11, or the alicyclic dicarboxylic acid diester compound according to any one of items 14 to 19 as a traction coefficient improver.

[Item 22]

A traction transmission comprising two or more rotors and the lubricant oil for power transmission according to item 12 or 13.

[Item 23]

A traction speed reducer comprising two or more rotors and the lubricant oil for power transmission according to item 12 or 13.

[Item 24]

A method for producing the alicyclic dicarboxylic acid diester compound represented by general formula (1), comprising reacting a dicarboxylic acid represented by general formula (2),

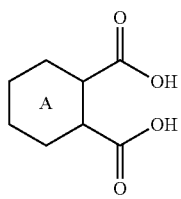

(2)

wherein ring A is as defined above, or an anhydride or dicarboxylic acid halide thereof with alcohol represented by general formula (3):

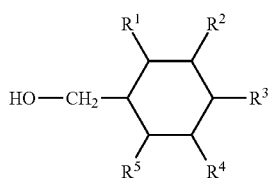

(3)

wherein $R^1$ to $R^5$ are as defined above.

Advantageous Effects of Invention

The alicyclic dicarboxylic acid diester compound of the present invention characteristically has a high traction coefficient and a high flash point, and thus can be suitably used as a lubricant base oil for power transmission (particularly a lubricant base oil for traction drives).

BRIEF DESCRIPTION OF DRAWINGS

FIG. 12 shows the $^{13}$C-NMR spectrum of the di(cyclohexylmethyl) 4-methyl-1,2-cyclohexanedicarboxylate obtained in Example 4.

heptane-2,3-dicarboxylate and di(3,4-dimethylcyclohexylmethyl) bicyclo[2.2.1]heptane-2,3-dicarboxylate obtained in Example 9.

Figure 27:
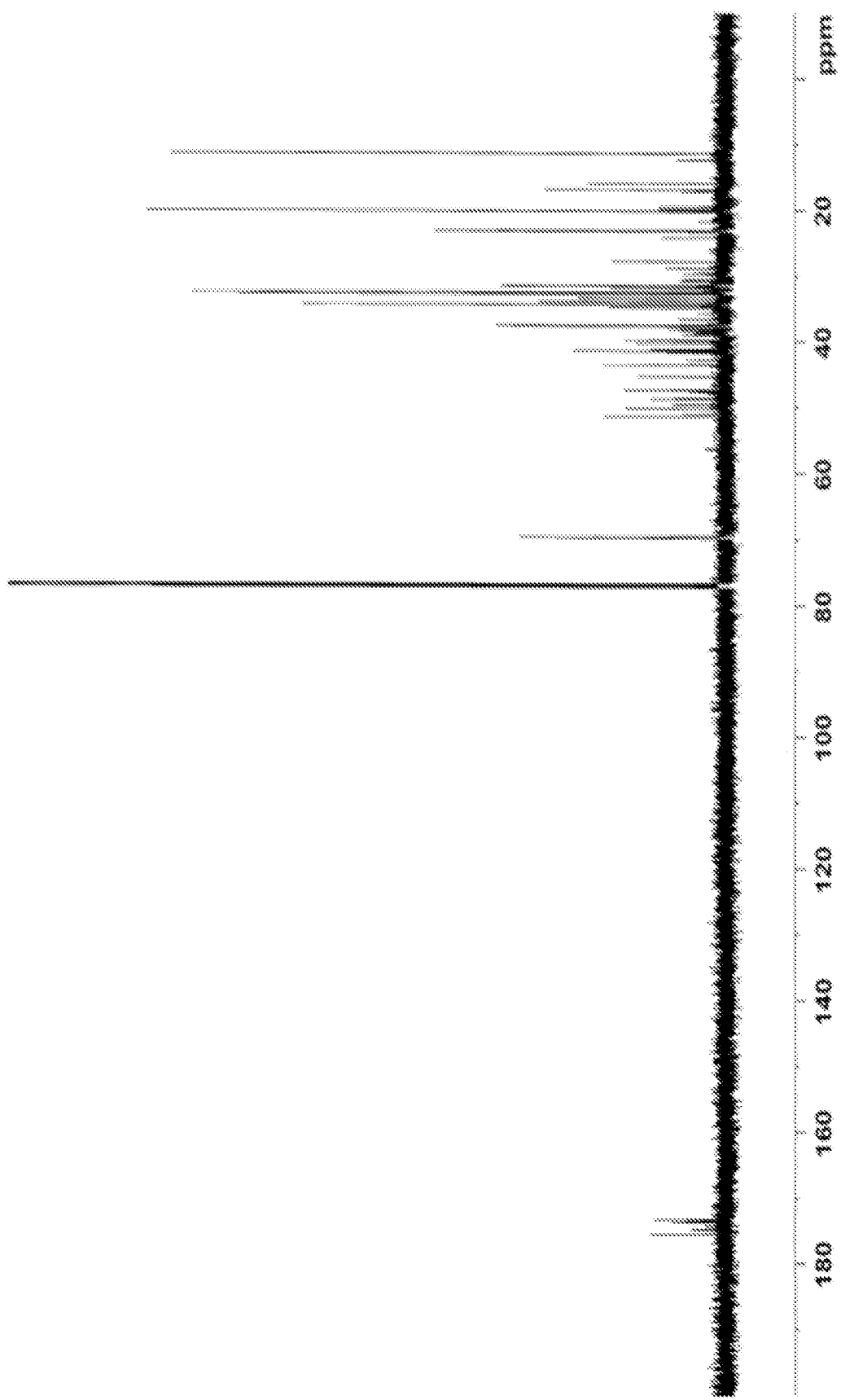

FIG. 27 shows the $^{13}$C-NMR spectrum of the mixture of di(3,4-dimethylcyclohexylmethyl) methylbicyclo[2.2.1] heptane-2,3-dicarboxylate and di(3,4-dimethylcyclohexylmethyl) bicyclo[2.2.1]heptane-2,3-dicarboxylate obtained in Example 9.

DESCRIPTION OF EMBODIMENTS

The lubricant base oil for power transmission of the present invention comprises an alicyclic dicarboxylic acid diester compound represented by general formula (1):

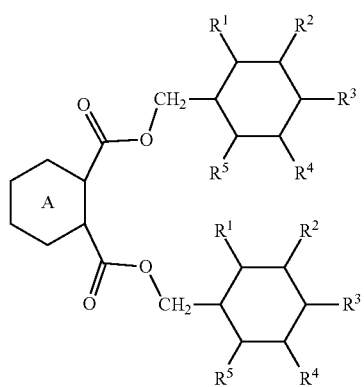
(1)

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; ring A is

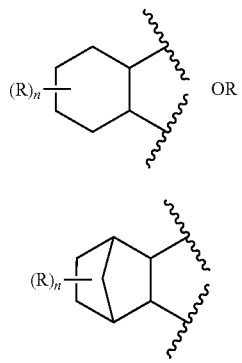
(i)

(ii)

wherein R represents $C_{1-3}$ alkyl, and n represents 0, 1, or 2; when n represents 2, R may be the same or different.

Examples of lubricant base oil for power transmission include a lubricant base oil for traction drives, a lubricant base oil for continuously variable transmissions, and the like. The lubricant base oil for power transmission is preferably a lubricant base oil for traction drives.

Examples of "linear or branched $C_{1-4}$ alkyl" represented by $R^1$ to $R^5$ include methyl, ethyl, n-propyl, isopropyl, n-butyl, isobutyl, sec-butyl, tert-butyl, and the like; and is preferably methyl.

Examples of "$C_{1-3}$ alkyl" represented by R include methyl, ethyl, n-propyl, isopropyl, and the like; and is preferably methyl.

n is 0, 1, or 2, and is preferably 0 or 1.

It is preferable that $R^1$ and $R^5$ are hydrogen, and it is more preferable that $R^1$, $R^2$, and $R^5$ are hydrogen.

It is preferable that $R^1$ and $R^5$ are hydrogen, and $R^2$, $R^3$, and $R^4$ are the same or different, and each represents hydrogen or linear or branched $C_{1-4}$ alkyl (in particular, methyl).

It is more preferable that $R^1$, $R^2$, and $R^5$ are hydrogen, and $R^3$ and $R^4$ are the same or different, and each represents hydrogen or linear or branched $C_{1-4}$ alkyl (in particular, methyl).

It is preferable that n is 0 or 1, and R is $C_{1-3}$ alkyl (in particular, methyl).

It is preferable that (a) R is $C_{1-3}$ alkyl (in particular, methyl) and n is 1 or 2; or (b) $R^3$ and/or $R^4$ is linear or branched $C_{1-4}$ alkyl (in particular, methyl).

It is more preferable that (a') R is $C_{1-3}$ alkyl (in particular, methyl) and n is 1; or (b') one of $R^3$ and $R^4$ is linear or branched $C_{1-4}$ alkyl (in particular, methyl), while the other is hydrogen, or both of $R^3$ and $R^4$ are linear or branched $C_{1-4}$ alkyl (in particular, methyl), and $R^1$, $R^2$, and $R^5$ are hydrogen.

Ring A is (i) or (ii), preferably (i), which is defined above.

In ring A, when n is 1, R is preferably bonded to the carbon atom at 3-Position or 4-Position with respect to the carbon atom bonded to the ester group of the cyclohexane ring. Specifically, when ring A is (i),

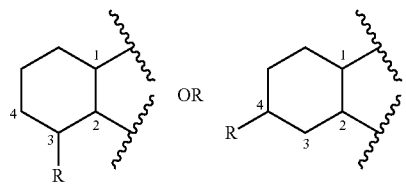

wherein R is as defined above,
and when ring A is (ii),

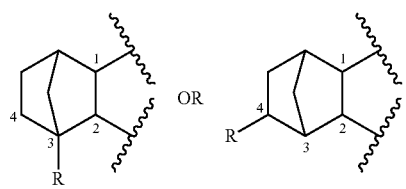

wherein R is as defined above.

In (i) and (ii), R is more preferably bonded to the carbon atom at 4-Position.

Examples of preferable compounds among the compounds represented by general formula (1) include a compound represented by general formula (1A):

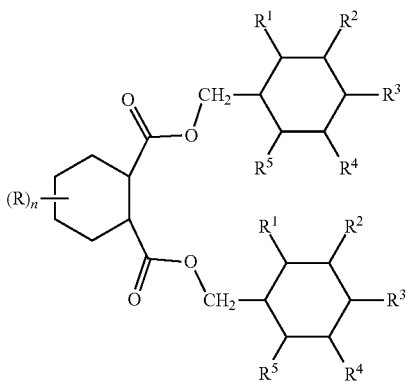

wherein R, n, and $R^1$ to $R^5$ are as defined above.

Other preferable examples include a compound represented by general formula (1B):

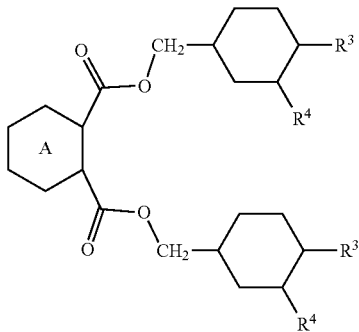

wherein ring A, $R^3$, and $R^4$ are as defined above.

Other preferable examples include a compound represented by general formula (1C):

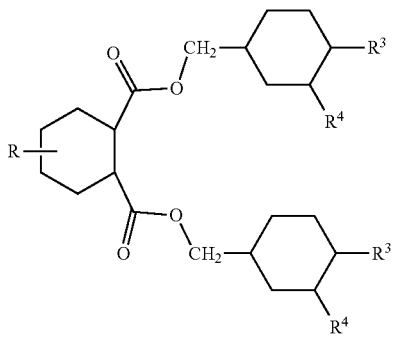

wherein R, $R^3$, and $R^4$ are as defined above.

Examples of alicyclic dicarboxylic acid diester compound represented by general formula (1) include di(cyclohexylmethyl) 1,2-cyclohexanedicarboxylate, di(4-methylcyclohexylmethyl) 1,2-cyclohexanedicarboxylate, di(4-methylcyclohexylmethyl) 1,2-cyclohexanedicarboxylate, di(4-n-propylcyclohexylmethyl) 1,2-cyclohexanedicarboxylate, di(4-isopropylcyclohexylmethyl) 1,2-cyclohexanedicarboxylate, di(4-n-butylcyclohexylmethyl) 1,2-cyclohexanedicarboxylate, di(4-tert-butylcyclohexylmethyl) 1,2-cyclohexanedicarboxylate, di(3,4-dimethylcyclohexylmethyl) 1,2-cyclohexanedicarboxylate, di(2,4-dimethylcyclohexylmethyl) 1,2-cyclohexanedicarboxylate, di(2,4,6-trimethylcyclohexylmethyl) 1,2-cyclohexanedicarboxylate, di(cyclohexylmethyl) 4-methylcyclohexane-1,2-dicarboxylate, di(4-methylcyclohexylmethyl) 4-methylcyclohexane-1,2-dicarboxylate, di(4-ethylcyclohexylmethyl) 4-methylcyclohexane-1,2-dicarboxylate, di(4-n-propylcyclohexylmethyl) 4-methylcyclohexane-1,2-dicarboxylate, di(4-isopropylcyclohexylmethyl) 4-methylcyclohexane-1,2-dicarboxylate, di(4-n-butylcyclohexylmethyl) 4-methylcyclohexane-1,2-dicarboxylate, di(4-tert-butylcyclohexylmethyl) 4-methylcyclohexane-1,2-dicarboxylate, di(3,4-dimethylcyclohexylmethyl) 4-methylcyclohexane-1,2-dicarboxylate, di(2,4-dimethylcyclohexylmethyl) 4-methylcyclohexane-1,2-dicarboxylate, di(2,4,6-trimethylcyclohexylmethyl) 4-methylcyclohexane-1,2-dicarboxylate, di(cyclohexylmethyl) 3-methylcyclohexane-1,2-dicarboxylate, di(4-methylcyclohexylmethyl) 3-methylcyclohexane-1,2-dicarboxylate, di(4-ethylcyclohexylmethyl) 3-methylcyclohexane-1,2-dicarboxylate, di(4-n-propylcyclohexylmethyl) 3-methylcyclohexane-1,2-dicarboxylate, di(4-isopropylcyclohexylmethyl) 3-methylcyclohexane-1,2-dicarboxylate, di(4-n-butylcyclohexylmethyl) 3-methylcyclohexane-1,2-dicarboxylate, di(4-tert-butylcyclohexylmethyl) 3-methylcyclohexane-1,2-dicarboxylate, di(3,4-dimethylcyclohexylmethyl) 3-methylcyclohexane-1,2-dicarboxylate, di(2,4-dimethylcyclohexylmethyl) 3-methylcyclohexane-1,2-dicarboxylate, di(2,4,6-trimethylcyclohexylmethyl) 3-methylcyclohexane-1,2-dicarboxylate, di(cyclohexylmethyl) bicyclo[2.2.1]heptane-2,3-dicarboxylate, di(4-methylcyclohexylmethyl) bicyclo[2.2.1]heptane-2,3-dicarboxylate, di(4-ethylcyclohexylmethyl) bicyclo[2.2.1]heptane-2,3-dicarboxylate, di(4-n-propylcyclohexylmethyl) bicyclo[2.2.1]heptane-2,3-dicarboxylate, di(4-isopropylcyclohexylmethyl) bicyclo[2.2.1]heptane-2,3-dicarboxylate, di(4-n-butylcyclohexylmethyl) bicyclo[2.2.1]heptane-2,3-dicarboxylate, di(4-tert-butylcyclohexylmethyl) bicyclo[2.2.1]heptane-2,3-dicarboxylate, di(3,4-dimethylcyclohexylmethyl) bicyclo[2.2.1]heptane-2,3-dicarboxylate, di(2,4-dimethylcyclohexylmethyl) bicyclo[2.2.1]heptane-2,3-dicarboxylate, di(2,4,6-trimethylcyclohexylmethyl) bicyclo[2.2.1]heptane-2,3-dicarboxylate, di(cyclohexylmethyl) methylbicyclo[2.2.1]heptane-2,3-dicarboxylate, di(4-methylcyclohexylmethyl) methylbicyclo[2.2.1]heptane-2,3-dicarboxylate, di(4-ethylcyclohexylmethyl) methylbicyclo[2.2.1]heptane-2,3-dicarboxylate, di(4-n-propylcyclohexylmethyl) methylbicyclo[2.2.1]heptane-2,3-dicarboxylate, di(4-isopropylcyclohexylmethyl) methylbicyclo[2.2.1]heptane-2,3-dicarboxylate, di(4-n-butylcyclohexylmethyl) methylbicyclo[2.2.1]heptane-2,3-dicarboxylate, di(4-tert-butylcyclohexylmethyl) methylbicyclo[2.2.1]heptane-2,3-dicarboxylate, di(3,4-dimethylcyclohexylmethyl) methylbicyclo[2.2.1]heptane-2,3-dicarboxylate, di(2,4-dimethylcyclohexylmethyl) methylbicyclo[2.2.1]heptane-2,3-dicarboxylate, and di(2,4,6-trimethylcyclohexylmethyl) methylbicyclo[2.2.1]heptane-2,3-dicarboxylate.

Among these, di(cyclohexylmethyl) 1,2-cyclohexanedicarboxylate, di(4-methylcyclohexylmethyl) 1,2-cyclohexanedicarboxylate, di(4-tert-butylcyclohexylmethyl) 1,2-cyclohexanedicarboxylate, di(3,4-dimethylcyclohexylmethyl) 1,2-cyclohexanedicarboxylate, di(2,4-dimethylcyclohexylmethyl) 1,2-cyclohexanedicarboxylate, di(2,4,6-trimethylcyclohexylmethyl) 1,2-cyclohexanedicarboxylate, di(cyclohexyl ethyl) 4-methylcyclohexane-1,2-dicarboxylate, di(4-methylcyclohexylmethyl) 4-methylcyclohexane-1,2-dicarboxylate, di(3,4-dimethylcyclohexylmethyl) 4-methylcyclohexane-1,2-dicarboxylate, di(2,4-dimethylcyclohexylmethyl) 4-methylcyclohexane-1,2-dicarboxylate, di(2,4,6-trimethylcyclohexyl ethyl) 4-methylcyclohexane-1,2-dicarboxylate, di(cyclohexylmethyl) bicyclo[2.2.1]heptane-2,3-dicarboxylate, di(4-methylcyclohexylmethyl) bicyclo[2.2.1]heptane-2,3-dicarboxylate, di(3,4-dimethylcyclohexylmethyl) bicyclo[2.2.1]heptane-2,3-dicarboxylate, di(2,4-dimethylcyclohexylmethyl) bicyclo[2.2.1]heptane-2,3-dicarboxylate, di(2,4,6-trimethylcyclohexylmethyl) bicyclo[2.2.1]heptane-2,3-dicarboxylate, di(cyclohexylmethyl) methylbicyclo[2.2.1]heptane-2,3-dicarboxylate, di(4-methylcyclohexylmethyl) methylbicyclo[2.2.1]heptane-2,3-dicarboxylate, di(3,4-dimethylcyclohexylmethyl) methylbicyclo[2.2.1]heptane-2,3-dicarboxylate, di(2,4-dimethylcyclohexylmethyl) methylbicyclo[2.2.1]heptane-2,3-dicarboxylate, and di(2,4,6-trimethylcyclohexylmethyl) methylbicyclo[2.2.1]heptane-2,3-dicarboxylate are preferable.

Further, di(cyclohexylmethyl) 1,2-cyclohexanedicarboxylate, di(cyclohexylmethyl) 4-methyl-1,2-cyclohexanedicarboxylate, di(4-methylcyclohexylmethyl) 1,2-cyclohexanedicarboxylate, di(3,4-dimethylcyclohexylmethyl) 1,2-cyclohexanedicarboxylate, di(4-methylcyclohexylmethyl) 4-methyl-1,2-cyclohexanedicarboxylate, di(3,4-dimethylcyclohexylmethyl) 4-methyl-1,2-cyclohexanedicarboxylate, di(cyclohexylmethyl) bicyclo[2.2.1]heptane-2,3-dicarboxylate, di(4-methylcyclohexylmethyl) bicyclo[2.2.1]heptane-2,3-dicarboxylate, di(3,4-dimethylcyclohexylmethyl) bicyclo[2.2.1]heptane-2,3-dicarboxylate, di(cyclohexylmethyl) methylbicyclo[2.2.1]heptane-2,3-dicarboxylate, di(4-methylcyclohexylmethyl) methylbicyclo[2.2.1]heptane-2,3-dicarboxylate, and di(3,4-dimethylcyclohexylmethyl) methylbicyclo[2.2.1]heptane-2,3-dicarboxylate are more preferable.

The above compounds may be used as a lubricant base oil for power transmission solely, or as a mixture of two or more kinds.

The method for producing the alicyclic dicarboxylic acid diester compound represented by general formula (1) is not particularly limited, as long as the compound is obtained. For example, the compound may be produced according to the following reaction formulas 1 to 3.

Reaction Formula 1

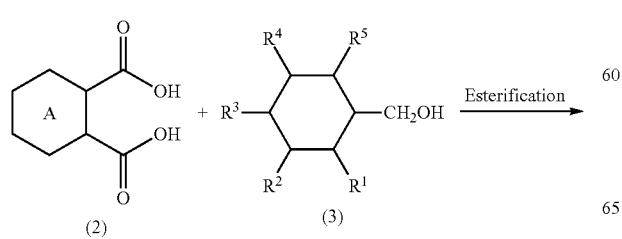

(2) + (3) → Esterification

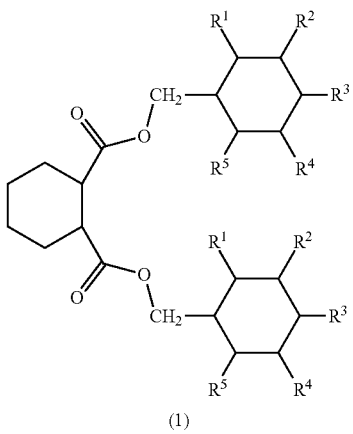

(1)

wherein ring A, and $R^1$ to $R^5$ are as defined above.

The compound represented by general formula (1) may be produced by an esterification reaction of the dicarboxylic acid represented by general formula (2), an anhydride or dicarboxylic acid halide thereof, and the alcohol represented by general formula (3). The dicarboxylic acid represented by general formula (2), an anhydride or dicarboxylic acid halide thereof, and the alcohol represented by general formula (3) may each include one or more compounds.

Reaction Formula 2

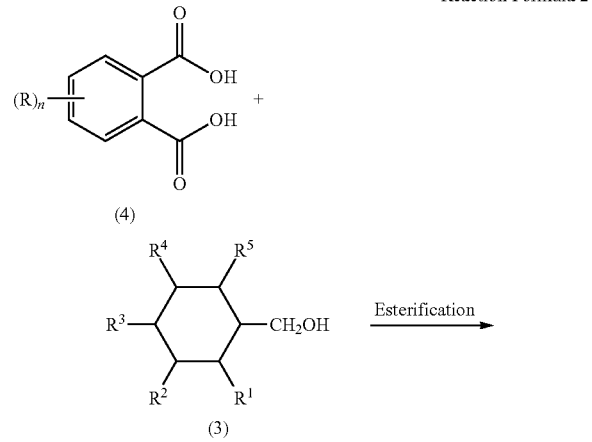

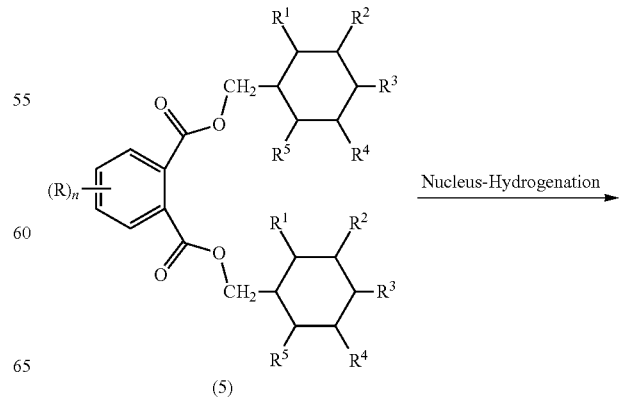

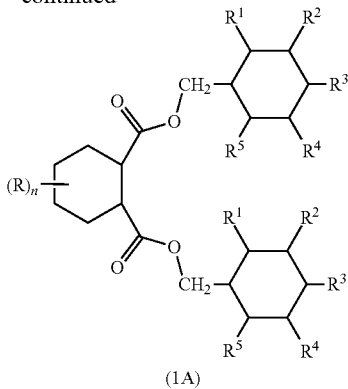

(1A)

wherein R, n, and $R^1$ to $R^5$ are as defined above.

By performing an esterification reaction of the dicarboxylic acid represented by general formula (4), an anhydride or dicarboxylic acid halide thereof, and the alcohol represented by general formula (3), the compound represented by general formula (5) can be produced. By further subjecting the benzene ring of the compound represented by general formula (5) to a nucleus-hydrogenation reaction (reduction reaction), the compound represented by general formula (1A) can be produced. The dicarboxylic acid represented by general formula (4), an anhydride or dicarboxylic acid halide thereof, and the alcohol represented by general formula (3) may each include one or more compounds.

Among the above production methods, the production method according to reaction formula 1 is preferable.

Since the esterification reactions of reaction formulas 1 and 2 can be performed by using similar reaction conditions, these reactions are summarized together below.

The esterification reactions according to reaction formulas 1 and 2 enables a reaction of a dicarboxylic acid, an anhydride or dicarboxylic acid halide thereof, with alcohol in the presence or absence of an esterification catalyst. The reaction may be performed by stirring under heat in an inert gas atmosphere, such as a nitrogen atmosphere.

Specific examples of the alicyclic dicarboxylic acid represented by general formula (2) include 1,2-cyclohexanedicarboxylic acid, 3-methylcyclohexane-1,2-dicarboxylic acid, 4-methylcyclohexane-1,2-dicarboxylic acid, bicyclo[2.2.1]heptane-2,3-dicarboxylic acid, methylbicyclo[2.2.1]heptane-2,3-dicarboxylic acid and the like. Among them, 4-methylcyclohexane-1,2-dicarboxylic acid is preferable. Alicyclic dicarboxylic acid derivatives, such as an anhydride or dicarboxylic acid halide thereof (in particular, dicarboxylic acid chloride), may also be used.

Specific examples of aromatic dicarboxylic acids (i.e., phthalic acid compound) represented by general formula (4) include phthalic acid, 3-methylphthalic acid, and 4-methylphthalic acid. Among these, 4-methylphthalic acid is preferable. Phthalic acid derivatives, such as an anhydride or dicarboxylic acid halide thereof (in particular, dicarboxylic acid chloride), may also be used.

Specific examples of alcohol (i.e., cyclohexylmethanol compound) represented by general formula (3) include cyclohexylmethanol, 4-methylcyclohexylmethanol, 4-ethylcyclohexylmethanol, 4-n-propylcyclohexylmethanol, 4-isopropylcyclohexylmethanol, 4-n-butylcyclohexylmethanol, 4-tert-butylcyclohexylmethanol, 3,4-dimethylcyclohexylmethanol, 2,4-dimethylcyclohexylmethanol, 2,4,6-trimethylcyclohexylmethanol, and the like. Among these, cyclohexylmethanol, 4-methylcyclohexylmethanol, 4-tert-butylcyclohexylmethanol, 3,4-dimethylcyclohexylmethanol, 2,4-dimethylcyclohexylmethanol, and 2,4,6-trimethylcyclohexylmethanol are preferable.

The amount of alcohol compound in the esterification reaction is, for example, generally 2 to 5 mole, preferably 2.01 to 3 mole, particularly 2.02 to 2.5 mole, per mole of the dicarboxylic acid compound (dicarboxylic acid, an anhydride or dicarboxylic acid halide thereof). In other words, the amount of alcohol compound is 1 to 2.5 equivalents, preferably 1.005 to 1.5 equivalents, particularly 1.01 to 1.25 equivalents, per equivalent of dicarboxylic acid compound.

Examples of catalyst used in the esterification reaction include mineral acids, organic acids, Lewis acids, and the like. More specifically, examples of mineral acids include sulfuric acid, hydrochloric acid, and phosphoric acid; examples of organic acids include p-toluenesulfonic acid, methanesulfonic acid, and the like; and examples of Lewis acids include aluminum compounds, tin compounds, titanium compounds, lead compounds, and zinc compounds. These compounds may be used solely, or in a combination of two or more kinds.

Among these, p-toluenesulfonic acid, $C_{3-8}$ tetraalkyltitanate, titanium oxide, titanium hydroxide, $C_{3-12}$ fatty acid tin, tin oxide, tin hydroxide, zinc oxide, zinc hydroxide, lead oxide, lead hydroxide, aluminum oxide, and aluminum hydroxide are particularly preferable. The amount of catalyst is, for example, 0.01 to 5 wt %, preferably 0.02 to 4 wt %, particularly 0.03 to 3 wt %, based on the total weight of the dicarboxylic acid compound or a derivative thereof and the alcohol compound, which are the materials of the esterification synthesis.

The reaction temperature is, for example, 100 to 230° C., and the esterification reaction is generally completed in 3 to 30 hours.

In the esterification reaction, a water-entraining agent (a solvent for removing water by an azeotropic reaction, an entraining reaction, or the like), such as benzene, toluene, xylene, or cyclohexane, can be used as necessary so as to accelerate the distillation of the water produced in the reaction as a by-product to the outside of the reaction system.

When oxygen is present during the esterification reaction, oxygen-containing organic compounds such as oxides, peroxides and carbonyl compounds are formed as a result of the oxidative degradation of the raw materials, the ester formed and the organic solvent (water-entraining agent). The generation of the oxygen-containing organic compounds may adversely affect the heat resistance, the weather resistance, and the like of the lubricant base oil containing an ester compound. In order to avoid such adverse effects, the reaction is preferably carried out in a reaction system in a nitrogen or other inert gas atmosphere or in an inert gas stream under atmospheric or reduced pressure.

The following step is exemplified as a post-treatment of the "crude esterified product" obtained after the reaction. Examples of post-treatment include a step of, under reduced or atmospheric pressure, distilling off excessive raw material and the like distillable under reduced or atmospheric pressure; when the crude esterified product contains residual carboxylic acid derived from the raw material and residual acid components derived from the esterification catalyst, a step of washing (neutralizing) the crude esterified product with an alkali aqueous solution, as well as washing it with water; a step of purification using extraction such as a liquid-liquid extraction; and a step of adsorptive purification using an adsorbent. By performing a post-treatment to purify the crude esterified product using an appropriate combination of these steps, it is possible to obtain an alicyclic dicarboxylic acid diester compound according to the present invention.

When the washing (neutralization) with an alkali aqueous solution is performed, a usable washing agent is, for example, sodium hydroxide, potassium hydroxide, lithium hydroxide, sodium carbonate, or like alkali aqueous solution. The alkali concentration of the aqueous solution is not particularly limited. For example, the alkali concentration is preferably about 0.5 to 20 wt %. The alkali aqueous solution is preferably used in an amount equal or appropriately excessive relative to the total acid value of the crude esterified product after the reaction. The washed product obtained after the alkali washing (neutralization) may be further washed with water, and the water-washing is preferably repeated until the water becomes neutral.

Examples of adsorbents used for the adsorptive purification include activated carbon, activated clay, activated alumina, hydrotalcite, silica gel, silica alumina, zeolite, magnesia, calcia, diatomaceous earth, and the like.

As shown in reaction formula 2, the nucleus-hydrogenation reaction of the benzene ring of the compound represented by general formula (5) to thereby obtain the compound represented by general formula (1A) may be performed in accordance with ordinary procedures. More specifically, this reaction may be performed under a hydrogen atmosphere in the presence of a hydrogenation catalyst.

Examples of hydrogenation catalysts include catalysts containing a base metal such as iron, cobalt, nickel, copper, or zinc; catalysts containing a noble metal such as rhodium, ruthenium, platinum, or palladium; and the like.

Examples of catalysts containing a base metal (hereinafter referred to as a base metal catalyst) include, in addition to the above base metals (zerovalent base metals), base metal salts (nitrates, sulfates, acetates, chlorides, bromides, and the like); base metal oxides; base metal hydroxides; base metal complex (acetylacetonate complex, amine complex, phosphine complex, carbonyl complex, and the like); and the like. These metals may be used as a catalyst solely, or in a combination of two or more kinds.

Examples of base metal catalysts further include base metal catalysts modified by adding one or more of boron, magnesium, aluminum, silicon, calcium, titanium, chromium, manganese, palladium, silver, tin, barium, molybdenum, and the like, to the above base metals.

These base metal catalysts may be used directly as a hydrogenation catalyst. Generally, in view of handling property and reactivity, sponge metal catalysts containing a base metal, or catalysts containing a base metal supported by a carrier (carrier-supported catalyst) may also be used.

Examples of sponge metal catalysts include many conventionally known or commercially available sponge metal catalysts, such as sponge nickel catalysts, sponge cobalt catalysts, sponge copper catalysts, sponge iron catalysts, sponge zinc catalysts, and the like. Among these, sponge nickel catalysts and sponge cobalt catalysts are preferable, and sponge nickel catalysts are particularly preferable in view of high selectivity.

Sponge metal catalysts are preferably those obtained by replacing moisture with an appropriate solvent in a water-containing sponge metal catalyst obtained by expanding a base metal. The solvent is not particularly limited insofar as it is compatible with water and does not adversely affect the product obtained by the nucleus-hydrogenation reaction of the present invention (such as ethylene glycol dimethyl ether).

Examples of carrier-supported catalysts include many conventionally known or commercially available catalysts, such as stabilized nickel catalysts, sulfur-resistant nickel catalysts, flake nickel catalysts, supported cobalt catalysts, and the like. Among these, stabilized nickel catalysts and sulfur-resistant nickel catalysts are preferable.

Examples of carriers used for the carrier-supported catalyst include diatomaceous earth, pumice, activated carbon, graphite, silica gel, alumina, magnesium oxide, zirconium oxide, titanium oxide, zeolite, calcium carbonate, barium sulfate, and the like. Among these, diatomaceous earth, alumina, and the like are preferable. These carriers may be used solely, or in a combination of two or more kinds.

The amount of the base metal catalyst to be supported in the carrier-supported catalyst is not particularly limited. The amount as the base metal catalyst is generally about 1 to 90 wt %, preferably 20 to 80 wt %, based on the total weight of the carrier-supported catalyst.

The method for producing these carrier-supported catalysts is not particularly limited. These catalysts may be easily produced, for example, by a conventionally known method such as impregnation, coprecipitation, or the like. Generally, commercially available catalysts may be used for the nucleus-hydrogenation either directly or after the catalysts are subjected to an appropriate activation treatment, such as reduction, before use.

The form of these base metal catalysts is not particularly limited; examples of the form include powder, tablet (molded catalyst), and the like. A suitable form may be selected among these forms according to the reaction method to be selected. Generally, powder-type catalysts are used for a hydrogenation reaction using a batch-wise or continuous suspended bed, and tablet-type catalysts (molded catalysts) are used for a hydrogenation reaction using a continuous fixed bed. Further, the shape and the size of the molded catalyst is suitably selected according to the size of the reactor to be used. A cylindrical molded catalyst having a diameter of 2 to 6 mm and a height of 2 to 8 mm is generally preferable.

The amount of the base metal catalysts to be used for the hydrogenation reaction is generally 0.1 to 50 wt %, preferably 0.5 to 20 wt %, particularly preferably 1 to 10 wt % as a base metal catalyst, based on the weight of the raw material. Within this range, the hydrogenation reaction may be performed at an economically advantageous and sufficient reaction rate.

Many conventionally known catalysts may be used as the catalyst containing a noble metal (hereinafter referred to as a noble metal catalyst). More specifically, examples of noble metal catalysts also include noble metals (zerovalent noble metals), noble metal salts (nitrates, sulfates, acetates, chlorides, bromides, and the like); noble metal oxides; noble metal hydroxides; noble metal complex (acetylacetonate complex, amine complex, phosphine complex, carbonyl complex, and the like), and the like. These metals may be used as a catalyst solely, or in a combination of two or more kinds.

These noble metal catalysts may be used directly as a hydrogenation catalyst. Generally, in view of handling property, reactivity, and selectivity, catalysts containing a noble metal supported by a carrier (carrier-supported catalysts) are preferably used. Conventionally known or commercially available carrier-supported catalysts may be used. Specific examples include catalysts in which a noble metal catalyst is supported by, as a carrier, diatomaceous earth, pumice, carbon (graphite, activated carbon, and the like), silica gel, alumina, hydrotalcite, barium sulfate, magnesium sulfate, zeolite, calcium carbonate, mixtures thereof, and the like. Among these, catalysts in which a noble metal catalyst is supported by a carbon or alumina (carbon-supported catalyst or aluminum-supported catalyst) are preferable in view of reactivity and selectivity.

The amount of the noble metal catalyst to be supported in the carrier-supported catalyst is not particularly limited. The amount as the noble metal catalyst is generally about 0.1 to 15 wt %, preferably 0.5 to 10 wt %, based on the total weight of the carrier-supported catalyst, in view of, for example, activity for each weight of the carrier-supported catalyst, or economic efficiency of the reaction step.

The amount of the noble metal catalyst to be used for the hydrogenation reaction is generally 0.005 to 20 wt %, preferably 0.01 to 10 wt %, based on the weight of the raw material.

The form of these noble metal catalysts is not particularly limited; examples of the form include powder, tablet, and the like depending on the reaction method to be selected. A suitable form may be selected among these forms. More specifically, powder-type catalysts are preferably used for a hydrogenation reaction using a batch-wise or continuous suspended bed, and tablet-type catalysts are preferably used for a hydrogenation reaction using a fixed bed.

The reaction temperature in the hydrogenation reaction may be appropriately set according to the type of catalyst, the amount of catalyst, hydrogen pressure, and the like. For example, the reaction temperature is preferably in a range of 50 to 280° C., particularly preferably 70 to 250° C. Hydrogen partial pressure in the hydrogenation reaction can be selected from a wide range; the hydrogen partial pressure is generally in a range of 0.5 to 20 MPa, particularly preferably in a range of 1 to 10 MPa. The reaction time may be appropriately set according to the type of catalyst, the amount of catalyst, and various other conditions; the reaction time is generally about 1 to 12 hours.

The reaction form may be a batch-wise reaction or a continuous reaction. Further, a fluidized bed or a fixed bed may be arbitrarily selected.

After the hydrogenation reaction is completed, the catalyst is isolated and removed by filtration under reduced or increased pressure, centrifugation, or other known methods; and an operation similar to the post-treatment for the crude esterified product above is optionally performed, thereby obtaining an alicyclic dicarboxylic acid diester compound represented by general formula (1) according to the present invention.

In the alicyclic dicarboxylic acid diester compound represented by general formula (1), stereoisomers, i.e., a trans-isomer and a cis-isomer, are present due to the steric configuration of the two ester groups. Further, when R is $C_{1-3}$ alkyl and n is 1 or 2, many more stereoisomers are present in addition to the trans-isomer and the cis-isomer of the ester groups, due to the steric configuration of R. The alicyclic dicarboxylic acid diester compound of the present invention may comprise a single stereoisomer or a mixture of many stereoisomers, insofar as the effects of the present invention are ensured.

The acid value of the alicyclic dicarboxylic acid diester compound is preferably 0.1 mg KOH/g or less, more preferably 0.05 mg KOH/g or less. When the acid value is 0.1 mg KOH/g or less, the heat resistance of the alicyclic dicarboxylic acid diester compound itself tends to increase. Such a preferable range also desirably influences the improvement in thermal oxidation stability of the base oil of the present invention. Examples of the method for reducing the acid value include a method of sufficiently advancing the reaction; a method performing neutralization with an alkali component, and washing with water (the step of washing (neutralizing) with an alkali aqueous solution and washing with water described above) during the post-treatment; and a method performing adsorption treatment using activated alumina.

The hydroxyl value of the alicyclic dicarboxylic acid diester compound is preferably 2 mg KOH/g or less, more preferably 1 mg KOH/g or less. When the hydroxyl value is 2 mg KOH/g or less, the hygroscopic property of the alicyclic dicarboxylic acid diester compound itself tends to further decrease, and the heat resistance tends to further increase. Such a preferable range also desirably influences the improvement in water resistance and thermal oxidation stability of the base oil of the present invention. Examples of the method for reducing the hydroxyl value include a method of sufficiently advancing the reaction, and a method of distilling off the alcohol component as a raw material under reduced pressure (the step of distilling off distillable excessive raw material and the like under reduced or atmospheric pressure described above) during the post-treatment.

The lubricant base oil for power transmission of the present invention may comprise other base oils (hereinafter referred to as "additional base oil") that can be added thereto. More specifically, the lubricant base oil for power transmission of the present invention encompasses only the alicyclic dicarboxylic acid diester compound represented by general formula (1), and a mixture of the alicyclic dicarboxylic acid diester compound and the additional base oil. Hereunder, the lubricant base oil for power transmission may also be referred to as a "base oil."

Examples of additional base oils include mineral oils (hydrocarbon oils obtained by purification of petroleum), poly-α-olefins, polybutenes, alkylbenzenes, alkylnaphthalenes, alicyclic hydrocarbon oils, isomerized oils of synthetic hydrocarbons obtained by the Fischer-Tropsch process and like synthetic hydrocarbon oils, animal and vegetable oils, organic acid esters other than the present ester; polyalkylene glycols; polyvinyl ethers; polyphenyl ethers; alkylphenyl ethers; silicone oils, and the like. At least one of these additional base oils may suitably be used.

Examples of mineral oils include solvent-refined mineral oils, mineral oils treated by hydrogenation, and wax isocerized oils; and usable mineral oils are those having a kinetic viscosity in the range of generally 1 to 25 mm/s, and preferably 2 to 20 mm²/s, at 100° C.

Examples of poly-α-olefins include polymers or copolymers of α-olefins having 2 to 16 carbon atoms (for example, ethylene, propylene, 1-butene, 1-hexane, 1-octene, 1-decene, 1-dodecene, 1-tetradecene, 1-hexadecene, etc.), the polymers or copolymers having a kinetic viscosity of 1 to 25 mm²/s at 100° C. and a viscosity index of 100 or more, and particularly preferably a kinetic viscosity of 1.5 to 20 mm²/s at 100° C. and a viscosity index of 120 or more.

Examples of polybutenes include those obtained by polymerizing isobutylene, or obtained by copolymerizing isobutylene with normal butylene; and those having a kinetic viscosity in the wide range of 2 to 40 mm²/s at 100° C. are generally usable.

Examples of alkylbenzenes include monoalkylbenzenes, dialkylbenzenes, trialkylbenzenes, tetraalkylbenzenes, and the like, with a molecular weight of 200 to 450, the alkyl(s) being linear or branched and having 1 to 40 carbon atoms.

Examples of alkylnaphthalenes include monoalkylnaphthalenes, dialkylnaphthalenes, and the like, the alkyl(s) being linear or branched and having 1 to 30 carbon atoms.

Examples of animal and vegetable oils include beef tallow, lard, palm oil, coconut oil, rapeseed oil, castor oil, sunflower oil, and the like.

Examples of organic acid esters include fatty acid monoesters, aliphatic dibasic acid diesters, aliphatic dihydric alcohol diesters, polyol esters, and other esters.

Examples of fatty acid monoesters include esters of a $C_5$-$C_{22}$ aliphatic linear or branched monocarboxylic acid, and a $C_3$-$C_{22}$ linear or branched saturated or unsaturated aliphatic alcohol.

Examples of aliphatic dibasic acid diesters include diesters of a $C_3$-$C_{22}$ linear or branched saturated or unsaturated aliphatic alcohol with an aliphatic dibasic acid such as oxalic acid, malonic acid, succinic acid, glutaric acid, adipic acid, pimelic acid, suberic acid, azelaic acid, sebacic acid, 1,9-nonamethylenedicarboxylic acid, 1,10-decamethylenedicarboxylic acid, etc.; or an anhydride thereof.

For aliphatic dihydric alcohol diesters and polyol esters, it is possible to use full esters of a polyol that has a neopentyl structure or a polyol that has a non-neopentyl structure with a $C_3$-$C_{22}$ linear or branched saturated or unsaturated fatty acid. Examples of polyols that have a neopentyl structure include neopentyl glycol, 2,2-diethylpropanediol, 2-butyl-2-ethylpropanediol, trimethylolethane, trimethylolpropane, pentaerythritol, ditrimethylolpropane, dipentaerythritol, and the like. Examples of polyols that have a non-neopentyl structure include 1,3-propanediol, 1,4-butanediol, 1,5-pentanediol, 1,6-hexanediol, 1,7-heptanediol, 1,8-octanediol, 1,9-nonanediol, 1,10-decanediol, 1,2-propanediol, 2-methyl-1,3-propanediol, 1,3-butanediol, 2-methyl-1,4-butanediol, 1,4-pentanediol, 2-methyl-1,5-pentanediol, 3-methyl-1,5-pentanediol, 1,5-hexanediol, 2-methyl-1,6-hexanediol, 3-methyl-1,6-hexanediol, 1,6-heptanediol, 2-methyl-1,7-heptanediol, 3-methyl-1,7-heptanediol, 4-methyl-1,7-heptanediol, 1,7-octanediol, 2-methyl-, 8-octanediol, 3-methyl-1,8-octanediol, 4-methyl-1,8-octanediol, 1,8-nonanediol, 2-methyl-1,9-nonanediol, 3-methyl-1,9-nonanediol, 4-methyl-1,9-nonanediol, 5-methyl-1,9-nonanediol, 2-ethyl-1,3-hexanediol, 2,4-diethyl-1,5-pentanediol, glycerin, polyglycerol, sorbitol, and the like.

Examples of other esters include esters of a polymerized fatty acid such as dimer acid or hydrogenated dimer acid, or a hydroxy fatty acid such as a condensed castor oil fatty acid or a hydrogenated condensed castor oil fatty acid, with a $C_3$-$C_{22}$ linear or branched saturated or unsaturated aliphatic alcohol.

Examples of polyalkylene glycols include a polymer prepared from an alcohol and one or more $C_2$-$C_4$ linear or branched alkylene oxides by ring-opening polymerization. Examples of alkylene oxides include ethylene oxide, propylene oxide, and butylene oxide; it is possible to use polymers prepared from one of these, or copolymers prepared from a mixture of two or more of these. It is also possible to use such compounds wherein the hydroxy group(s) at one or both ends are etherified. The kinetic viscosity of the polymer is preferably 5 to 1000 mm$^2$/s (40° C.), more preferably 5 to 500 mm$^2$/s (40° C.).

Polyvinyl ethers are compounds obtained by polymerizing a vinyl ether monomer. Examples of monomers include methyl vinyl ether, ethyl vinyl ether, isopropyl vinyl ether, n-butyl vinyl ether, isobutyl vinyl ether, sec-butyl vinyl ether, tert-butyl vinyl ether, n-pentyl vinyl ether, n-hexyl vinyl ether, 2-methoxyethyl vinyl ether, 2-ethoxyethyl vinyl ether, and the like. The kinetic viscosity of the polymer is preferably 5 to 1000 m/s (40° C.), and more preferably 5 to 500 mm$^2$/s (40° C.).

Examples of polyphenyl ethers include compounds having a structure wherein the meta positions of two or more aromatic rings are connected by ether linkages or thioether linkages; specifically, for example, bis(m-phenoxyphenyl) ether, m-bis(m-phenoxyphenoxy)benzene, and thioethers (so-called C-ethers) wherein one or more oxygen atoms thereof are replaced by one or more sulfur atoms.

Examples of alkylphenyl ethers include compounds wherein a polyphenyl ether is substituted with $C_6$-$C_{18}$ linear or branched alkyl group(s); in particular, alkyldiphenyl ethers substituted with one or more alkyl groups are preferable.

Examples of silicone oils include dimethyl silicone and methylphenyl silicone; and also include long-chain alkyl silicone, fluorosilicone, and like modified silicones.

The content of the alicyclic dicarboxylic acid diester compound represented by general formula (1) in the lubricant base oil for power transmission of the present invention is generally 70 wt % or more, preferably 80 wt % or more, more preferably 90 wt % or more.

The content of the additional base oil in the lubricant base oil for power transmission of the present invention is generally 30 wt % or less, preferably 20 wt % or less, more preferably 10 wt % or less.

The traction coefficient (60° C.) of the lubricant base oil for power transmission of the present invention is 0.095 or more, preferably 0.1 or more. The traction coefficient (60° C.) in the present specification and claims is a value measured according to the method described in the Examples shown below.

The kinetic viscosity (100° C.) of the lubricant base oil for power transmission of the present invention is generally 4 to 25 mm$^2$/s, preferably 4 to 20 m&/s, more preferably 5 to 20 mm$^2$/s. The kinetic viscosity (100° C.) in the present specification and claims is a value measured according to the method described in the Examples shown below.

The kinetic viscosity (40° C.) of the lubricant base oil for power transmission of the present invention is generally 50 to 1000 mm$^2$/s, preferably 100 to 800 mm$^2$/s. The kinetic viscosity (40° C.) in the present specification and claims is a value measured according to the method described in the Examples shown below.

The pour point of the lubricant base oil for power transmission of the present invention is generally 3° C. or less, preferably 1° C. or less, more preferably −5° C. or less, particularly preferably −10° C. or less, in view of operability at a low temperature. The pour point in the present specification and claims is a value measured according to the method described in the Examples shown below.

The flash point of the lubricant base oil for power transmission of the present invention is generally 210° C. or more, preferably 215° C. or more, particularly preferably 220 to 260° C., in view of storage stability. The flash point in the present specification and claims is a value measured according to the method described in the Examples shown below.

The present invention also provides a lubricant oil for power transmission comprising the lubricant base oil for power transmission. In order to improve its performance, the lubricant oil for power transmission may suitably comprise, in addition to the base oil, at least one additive selected from the group consisting of antioxidants, metal detergents, ashless dispersants, oiliness agents, antiwear agents, extreme-pressure agents, metal deactivators, rust inhibitors, viscosity index improvers, pour point depressants, antifoaming agents, hydrolysis inhibitors, thickeners, corrosion inhibitors, and hue stabilizers. The amounts of such additives are not particularly limited as long as the effects of the present invention are ensured, and specific examples are as described below.

Examples of antioxidants include 2,6-di-tert-butylphenol, 2,6-di-tert-butyl-p-cresol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3,5-di-tert-butyl-4-hydroxyphenyl) propionate]m ethane, 1,1,3-tris(2-methyl-4-hydroxy-5-tert-butylphenyl) butane, 1,3,5-trimethyl-2,4,6-tris(3,5-di-tert-butyl-4-hydroxybenzyl)benzene, 2,2'-dihydroxy-3,3'-di(α-methylcyclohexyl)-5,5'-dimethyl-diphenylmethane, 2,2'-isobutylidenebis(4,6-dimethylphenol), 2,6-bis(2'-hydroxy-3'-tert-butyl-5'-methylbenzyl)-4-methylphenol, 1,1'-bis(4-hydroxyphenyl)cyclohexane, 2,5-di-tert-amylhydroquinone, 2,5-di-tert-butylhydroquinone, 1,4-dihydroxyanthraquinone, 3-tert-butyl-4-hydroxyanisole, 2-tert-butyl-4-hydroxyanisole, 2,4-dibenzoylresorcinol, 4-tert-butylcatechol, 2,6-di-tert-butyl-4-ethylphenol, 2-hydroxy-4-methoxybenzophenone, 2,4-dihydroxybenzophenone, 2,2'-dihydroxy-4-methoxybenzophenone, 2,4,5-trihydroxybenzophenone, α-tocopherol, bis[2-(2-hydroxy-5-methyl-3-tert-butylbenzyl)-4-methyl-6-tert-butylphenyl]terephthalate, triethyleneglycol bis[3-(3-tert-butyl-5-methyl-4-hydroxyphenyl) propionate], 1,6-hexanediol-bis[3-(3,5-di-tert-butyl-4-hydroxyphenyl)propionate]; diphenylamines such as diphenylamine, monobutyl (including linear and branched) diphenylamines, monopentyl (including linear and branched) diphenylamines, monohexyl (including linear and branched) diphenylamines, monoheptyl (including linear and branched) diphenylamines, monooctyl (including linear and branched) diphenylamines, and like monoalkyl diphenylamines, in particular, mono($C_4$-$C_9$ alkyl)diphenylamines (i.e., diphenylamines wherein one of the two benzene rings is mono-substituted with an alkyl group, in particular, a $C_4$-$C_9$ alkyl group, i.e., a monoalkyl-substituted diphenylamines), p,p'-dibutyl (including linear and branched) diphenylamines, p,p'-dipentyl (including linear and branched) diphenylamines, p,p'-dihexyl (including linear and branched) diphenylamines, p,p'-diheptyl (including linear and branched) diphenylamines, p,p'-dioctyl (including linear and branched) diphenylamines, p,p'-dinonyl (including linear and branched) diphenylamines, and like di(alkylphenyl)amines, in particular, p,p'-di($C_4$-$C_9$ alkylphenyl) amines (i.e., dialkyl-substituted diphenylamines wherein each of the two benzene rings is mono-substituted with an alkyl group, in particular, a $C_4$-$C_9$ alkyl group, and the two alkyl groups are identical), di(mono $C_4$-$C_9$ alkylphenyl) amines wherein the alkyl group on one of the benzene rings is different from the alkyl group on the other of the benzene rings, di(di-$C_4$-$C_9$ alkylphenyl)amines wherein at least one of the four alkyl groups on the two benzene rings is different from the rest of the alkyl groups; naphthylamines such as N-phenyl-1-naphthylamine, N-phenyl-2-naphthylamine, 4-octylphenyl-1-naphthylamine, and 4-octylphenyl-2-naphthylamine; phenylenediamines such as p-phenylenediamine, N-phenyl-N'-isopropyl-p-phenylenediamine, and N-phenyl-N'-(1,3-dimethylbutyl)-p-phenylenediamine; and the like.

Among these, in particular, p,p'-dioctyl (including linear and branched) diphenylamines, p,p'-dinonyl (including linear and branched) diphenylamines, N-phenyl-1-naphthylamine, di(n-dodecyl) thiodipropionate, di(n-octadecyl) thiodipropionate and like thiodipropionic acid esters; phenothiazine and like sulfur-based compounds; etc., can be given as preferable examples. These antioxidants may be used singly, or in a combination of two or more kinds. When such antioxidants are used, the amount thereof is generally about 0.01 to 5 wt %, and preferably about 0.05 to 3 wt %, based on the base oil.

The present specification and claims may occasionally define the range of additive content by using the phrase "based on the base oil," such as in the expression "0.01 to 5 wt % based on the base oil." The term "base oil" used herein means either a base oil consisting only of the alicyclic dicarboxylic acid diester compound according to the present invention, or a base oil constituted of a mixture of the alicyclic dicarboxylic acid diester compound and an additional base oil. Further, for example, the expression "0.01 to 5 wt % based on the base oil" is equivalent to "0.01 to 5 parts by weight based on 100 parts by weight of the base oil."

Examples of usable metal detergents include Ca-petroleum sulfonates, overbased Ca-petroleum sulfonates, Ca-alkylbenzene sulfonates, overbased Ca-alkylbenzene sulfonates, Ba-alkylbenzene sulfonates, overbased Ba-alkylbenzene sulfonates, Mg-alkylbenzene sulfonates, overbased Mg-alkylbenzene sulfonates, Na-alkylbenzene sulfonates, overbased Na-alkylbenzene sulfonates, Ca-alkylnaphthalene sulfonates, overbased Ca-alkylnaphthalene sulfonates, and like metal sulfonates; Ca-phenate, overbased Ca-phenate, Ba-phenate, overbased Ba-phenate, and like metal phenates; Ca-salicylate, overbased Ca-salicylate and like metal salicylates; Ca-phosphonate, overbased Ca-phosphonate, Ba-phosphonate, overbased Ba-phosphonate, and like metal phosphonates; overbased Ca-carboxylates; and the like. When such metal detergents are used, the amount thereof is generally about 1 to 10 wt %, and preferably about 2 to 7 wt %, based on the base oil.

Examples of ashless dispersants include polyalkenyl succinimides, polyalkenyl succinamides, polyalkenyl benzylamines, polyalkenyl succinic acid esters, and the like. These ashless dispersants can be used singly, or in combination. When such ashless dispersants are used, the amount thereof is generally about 1 to 10 wt %, and preferably about 2 to 7 wt %, based on the base oil.

Examples of oiliness agents include stearic acid, oleic acid, and like saturated or unsaturated aliphatic monocarboxylic acids; dimer acid, hydrogenated dimer acid, and like polymerized fatty acids; ricinoleic acid, 12-hydroxystearic acid, and like hydroxyfatty acids; lauryl alcohol, oleyl alcohol, and like saturated or unsaturated aliphatic monoalcohols; stearyl amine, oleyl amine, and like saturated or unsaturated aliphatic monoamines; lauramide, oleamide, and like saturated or unsaturated aliphatic monocarboxylic acid amides; batyl alcohol, chimyl alcohol, selachyl alcohol, and like glycerin ethers; lauryl polyglycerol ether, oleyl polyglyceryl ether, and like alkyl or alkenyl polyglyceryl ethers; di(2-ethyihexyl)monoethanolamine, diisotridecyl monoethanolamine, and like poly(alkylene oxide) adducts of alkyl or alkenylamine; and the like. These oiliness agents can be used singly, or in combination. When such oiliness agents are used, the amount thereof is generally about 0.01 to 5 wt %, and preferably about 0.1 to 3 wt %, based on the base oil.

Examples of antiwear agents and extreme-pressure agents include phosphorus-based compounds such as tricresyl phosphate, cresyldiphenyl phosphate, alkylphenyl phosphates, tributyl phosphate, dibutyl phosphate and like phosphoric acid esters, tributyl phosphite, dibutyl phosphite, triisopropyl phosphite and like phosphorous acid esters, as well as amine salts thereof; sulfur-based compounds such as sulfurized oils and fats, sulfurized oleic acid and like sulfurized fatty acids, di-benzyl disulfide, sulfurized olefins, and dialkyl disulfides; organometallic compounds such as Zn-dialkyldithio phosphates, Mo-dialkyldithio phosphates, and Mo-dialkyldithio carbamates; and the like. These antiwear agents can be used singly, or in combination. When such antiwear agents are used, the amount thereof is generally about 0.01 to 10 wt %, and preferably about 0.1 to 5 wt %, based on the base oil.

Examples of metal deactivators include benzotriazole-based compounds, thiadiazole-based compounds, gallic acid ester-based compounds, and the like. These metal deactivators can be used singly, or in combination. When such metal deactivators are used, the amount thereof is generally about 0.01 to 0.4 wt %, and preferably about 0.01 to 0.2 wt %, based on the base oil.

Examples of rust inhibitors include dodecenylsuccinic acid half-esters, octadecenylsuccinic anhydride, dodecenylsuccinic amide, and like alkyl or alkenyl succinic acid derivatives; sorbitan monooleate, glycerol monooleate, pentaerythritol monooleate, and like partial esters of polyhydric alcohols; Ca-petroleum sulfonate, Ca-alkylbenzene sulfonates, Ba-alkylbenzene sulfonates, Mg-alkylbenzene sulfonates, Na-alkylbenzene sulfonates, Zn-alkylbenzene sulfonates, Ca-alkylnaphthalene sulfonates, and like metal sulfanates; rosin amine, N-oleyl sarcosine, and like amines; dialkyl phosphite amine salts; and the like. These rust inhibitors can be used singly, or in combination. When such rust inhibitors are used, the amount thereof is generally about 0.01 to 5 wt %, and preferably about 0.05 to 2 wt %, based on the base oil.

Examples of viscosity index improvers include polyalkylmethacrylates, polyalkylstyrenes, polybutenes, ethylene-propylene copolymers, styrene-diene copolymers, styrene-maleic anhydride ester copolymers, and like olefin copolymers. These viscosity index improvers can be used singly, or in combination. When such viscosity index improvers are used, the amount thereof is generally about 0.1 to 15 wt %, and preferably about 0.5 to 7 wt %, based on the base oil.

Examples of pour point depressants include condensates of chlorinated paraffin and alkylnaphthalene; condensates of chlorinated paraffin and phenol; and polyalkylmethacrylates, polyalkylstyrenes, polybutenes, etc., which are also viscosity index improvers as mentioned above. These pour point depressants can be used singly, or in combination. When such pour point depressants are used, the amount thereof is generally about 0.01 to 5 wt %, and preferably about 0.1 to 3 wt %, based on the base oil.

Liquid silicones are suitable as an antifoaming agent. When such antifoaming agents are used, the amount thereof is generally about 0.0005 to 0.01 wt %, based on the base oil.

Examples of usable hydrolysis inhibitors include alkyl glycidyl ethers; alkyl glycidyl esters; alkylene glycol glycidyl ethers; alicyclic epoxides; phenyl glycidyl ether and like epoxy compounds; and di-tert-butylcarbodiimide, 1,3-di-p-tolylcarbodiimide, and like carbodiimide compounds. The amount is generally about 0.05 to 2 wt %, based on the base oil.

A "grease" may be produced by suitably combining a thickener with the lubricant base oil for traction drives of the present invention.

Examples of thickeners include soap-based thickeners such as sodium soap, lithium soap, calcium soap, calcium complex soap, aluminum complex soap, or lithium complex soap; nonsoap thickeners such as bentonite, silica aerogel, sodium terephthalamate, urea compound, polytetrafluoroethylene, or boron nitride; and the like.

Examples of metal soap-based thickeners include hydroxy-containing aliphatic carboxylic acid lithium salts, such as lithium 12-hydroxystearate; aliphatic carboxylic acid lithium salts such as lithium stearate; and mixtures thereof.

Examples of metal complex soap-based thickeners include complexes of hydroxy-containing monovalent aliphatic carboxylic acid metal salt and divalent aliphatic carboxylic acid metal salt, and the like. Specifically, a lithium complex soap and an aluminum complex soap are exemplified.

Examples of urea compounds include alicyclic, aromatic, aliphatic, diurea, triurea, tetraurea, urea-urethane compounds, and the like.

Among these, lithium soap, lithium complex soap, and urea compounds are preferable as a thickener. Urea compounds are particularly preferable in terms of heat resistance.

These thickeners may be used solely, or in a suitable combination of two or more kinds. The addition amount of the thickener is not particularly limited as long as the predetermined effects are ensured.

Examples of corrosion inhibitors include sodium sulfonate and sorbitan ester. The corrosion inhibitor is generally added in an amount of about 0.1 to 3.0 wt % based on the base oil.

Examples of hue stabilizers include substituted hydroquinones, furfural azine, and the like. The hue stabilizer is generally added in an amount of about 0.01 to 0.1 wt % based on the base oil.

As described above, the lubricant oil for power transmission of the present invention thus obtained is suitable for a lubricant oil for traction drives, because it comprises a base oil having a high traction coefficient and a high flash point.

By adding the lubricant base oil for power transmission of the present invention and the alicyclic dicarboxylic acid diester compound represented by general formula (1) to a lubricant oil for power transmission (in particular, a lubricant oil for traction drives), it is possible to increase the traction coefficient of the lubricant oil for power transmission. Therefore, they may also be used as a traction coefficient improver.

Due to its high power transmission performance, low vibration or noise, as well as high flash point, the lubricant oil for power transmission of the present invention may be used as a lubricant oil for traction drives, i.e., power transmission apparatuses constituted of two or more rotors. Examples of the apparatus in which the traction drive is adopted include motors, transmissions, generators, speed reducers, and the like for vehicles, marine vessels, aircraft, precision equipment, robots, and the like.

EXAMPLES

The present invention is described in detail below with reference to Examples; however, the present invention is not limited thereto. The methods for measuring characteristics in the Examples and Comparative Examples are as described below. Commercially available reagents were used as compounds that were not specified.

Neutralization Value (NV)

Measurement was performed according to JIS K2501 (2003).

Acid Value (AV)

The acid value of the alicyclic dicarboxylic acid diester compounds was measured according to JIS K2501 (2003).

Hydroxyl Value (OHV)

The hydroxyl value of the alicyclic dicarboxylic acid diester compounds was measured according to JIS K0070 (1992).

Traction Coefficient

The maximum traction coefficient was measured as the traction coefficient (60° C.) when the base oils were tested using the following apparatus under the following conditions.

Measurement Conditions

Apparatus: ball-on-ring wear tester (model TE54, produced by Phoenix Tribology)
Test piece shape: upper test piece (25-mm-diameter sphere), lower test piece (50-mm-diameter ring)
Test piece material: SUJ2
Rotational speed: 1.0 to 1.5 mm/s
Slip ratio: 0.5 to 50% (changed every 0.5%)
Sample temperature: 60° C.
Load: 100 N Method for Measuring Kinetic Viscosity The kinetic viscosity of the base oils at 40° C. and 100° C. was measured according to JIS K2283 (2000).

Low-Temperature Fluidity Test Using Method for Measuring Pour Point

The pour point of the base oils was measured according to JIS K2269 (1987)

Flash Point

The flash point of the base oils was measured according to JIS K2265 (Cleveland open cup method).

IR Spectra

The IR spectra of the alicyclic dicarboxylic acid diester compounds were measured by ATR (attenuated total reflection) spectroscopy using an infrared spectroscopic analyzer (Spectrum 400, produced by PerkinElmer Japan Co., Ltd.).

Proton Nuclear Magnetic Resonance Spectra ($^1$H-NMR)

$^1$H-NMR (300 MHz, heavy chloroform) of the alicyclic dicarboxylic acid diester compounds was measured using a nuclear magnetic resonance apparatus (JNM-AL300, produced by JEOL Ltd.).

Carbon Nuclear Magnetic Resonance Spectra ($^{13}$C-NMR)

$^{13}$C-NMR (75 MHz, heavy chloroform) of the alicyclic dicarboxylic acid diester compounds was measured using a nuclear magnetic resonance apparatus (JNM-AL300, produced by JEOL Ltd.).

Used Compounds 1,2-Cyclohexanedicarboxylic anhydride (product name: "Rikacid HH," produced by New Japan Chemical Co., Ltd.); neutralization value: 727 (hereinafter referred to as "HH")

4-Methyl-1,2-cyclohexanedicarboxylic anhydride (product name: "Rikacid MH," produced by New Japan Chemical Co., Ltd.); neutralization value: 666 (hereinafter referred to as "MH")

Mixture of methylbicyclo[2.2.1]heptane-2,3-dicarboxylic anhydride and bicyclo[2.2.1]heptane-2,3-dicarboxylic anhydride (when the amount of the entire mixture is 100 wt. %, the former is 75 to 85 wt. % and the latter is 25 to 15 wt. %) (product name: "Rikacid HNA-100," produced by New Japan Chemical Co., Ltd.); neutralization value: 638 (hereinafter referred to as "HNA")

Cyclohexylmethanol (product name: "Cyclohexane Methanol," produced by Tokyo Chemical Industry Co., Ltd.) (hereinafter referred to as "CHM")

2-Ethylhexanol (product name: "Octanol," produced by KH Neochem Co., Ltd.) (hereinafter referred to as "2EH")

n-Octanol (product name: "Conol 10WS," produced by New Japan Chemical Co., Ltd.) (hereinafter referred to as "nC8")

Diisodecyl adipate (product name: "SANSO CIZER DIDA," produced by New Japan Chemical Co., Ltd.) (hereinafter referred to as "DIDA")

Mineral oil Y: industrial liquid paraffin of saturated hydrocarbon (product name: "Yubase 3," produced by SK Lubricants Co., Ltd.) (hereinafter referred to as "YUBASE")

Cyclohexylmethanol compounds were synthesized by the following production method.

Production Example 1:
4-methylcyclohexylmethanol 3,000 g of 4-methylbenzaldehyde (product name: "Para-Tolualdehyde," produced by Mitsubishi Gas Chemical Company, Inc.) and 150 g of ruthenium catalyst carried on alumina were placed in a 6.4-L autoclave, and the mixture was heated to 100° C. Thereafter, hydrogenation reaction was performed in a hydrogen atmosphere at 5 MPa for 10 hours. After cooling to room temperature, the catalyst was removed by filtration, and distillation was performed, thereby obtaining 1,550 g of 4-methylcyclohexylmethanol (hereinafter referred to as "4-MCHM").

Production Example 2:
3,4-dimethylcyclohexylmethanol

The reaction was performed in the same manner as in Production Example 1, except that the 4-methylbenzaldehyde was changed to 3,4-dimethylbenzaldehyde (product name: "3,4-Dimethylbenzaldehyde," produced by Mitsubishi Gas Chemical Company, Inc.), and the reaction temperature was changed to 120° C., thereby obtaining 1,020 g of 3,4-dimethylcyclohexylmethanol (hereinafter referred to as "3,4-MCHM").

Example 1

508.7 g (3.3 mol) of 1,2-cyclohexanedicarboxylic anhydride as alicyclic dicarboxylic acid, 829.0 g (7.26 mol) of cyclohexylmethanol, and 1.2 g of tin oxide as an esterification catalyst were placed in a 2-L four-necked flask equipped with a stirrer, a thermometer, and a water fraction receiver with a cooling pipe. After the inside of the flask was purged with nitrogen, the mixture was gradually heated to 230° C. Esterification reaction was performed while removing distilled water using the water fraction receiver with reference to the theoretical water amount (59.4 g), and adjusting the decompression degree so that the cyclohexylmethanol refluxed. The reaction was performed until the acid value became 0.2 mg KOH/g or less. After completion of the reaction, the remaining cyclohexylmethanol was removed by distillation under reduced pressure to obtain a crude esterified product.

After neutralization with a caustic soda aqueous solution in an amount of 3-fold equivalents relative to the acid value of the obtained crude esterified product, water-washing was repeated until it became neutral. After dehydration was carried out by adding magnesium sulfate to the obtained crude esterified product, the magnesium sulfate was removed by filtration, thereby obtaining 1097.2 g (3.01 mol) of di(cyclohexylmethyl) 1,2-cyclohexanedicarboxylate. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (A) Table 1 shows the results.

Figure 1:
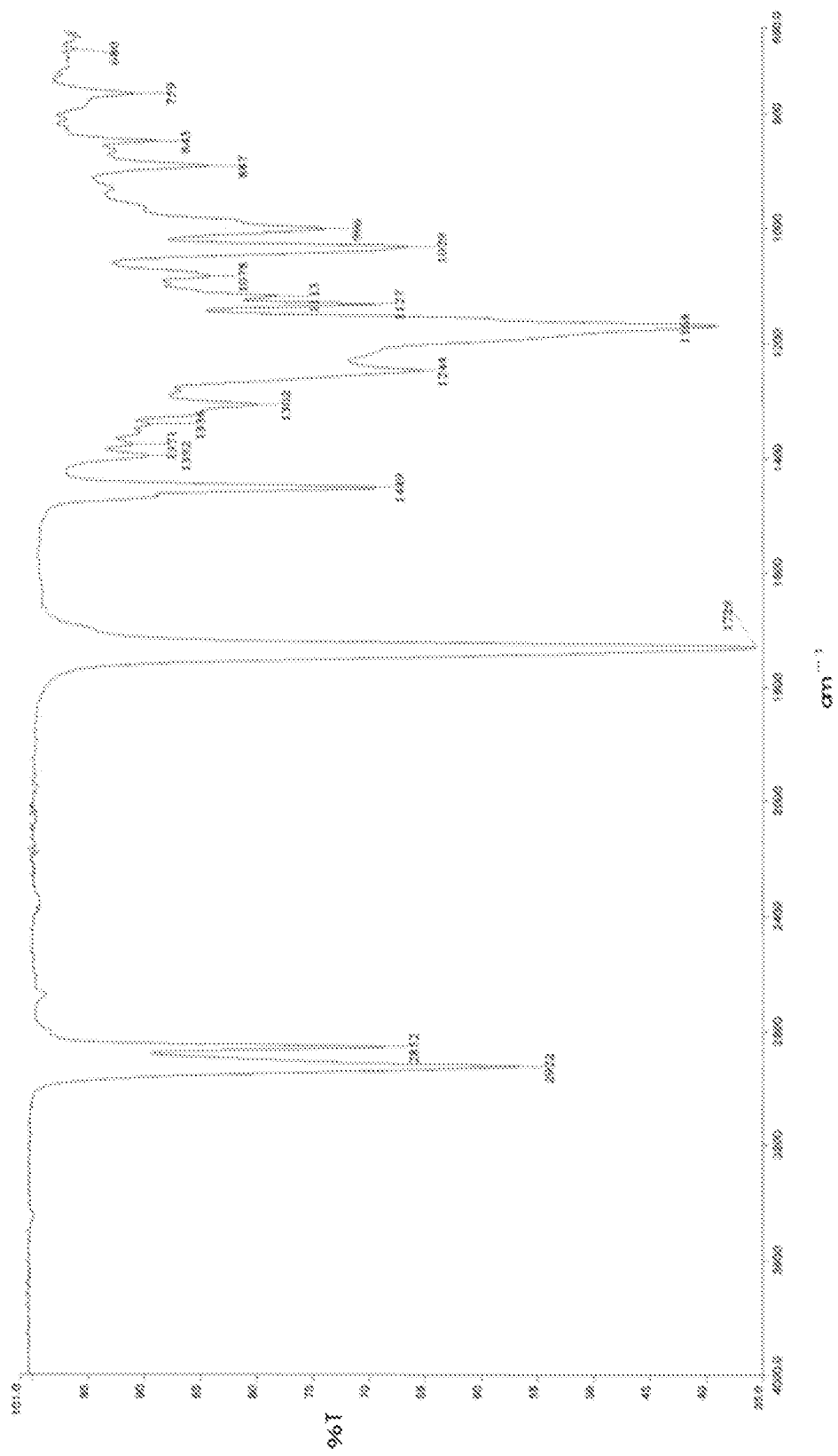
FIG. 1 shows the IR spectrum of the di(cyclohexylmethyl) 1,2-cyclohexanedicarboxylate obtained in Example 1.
Figure 2:
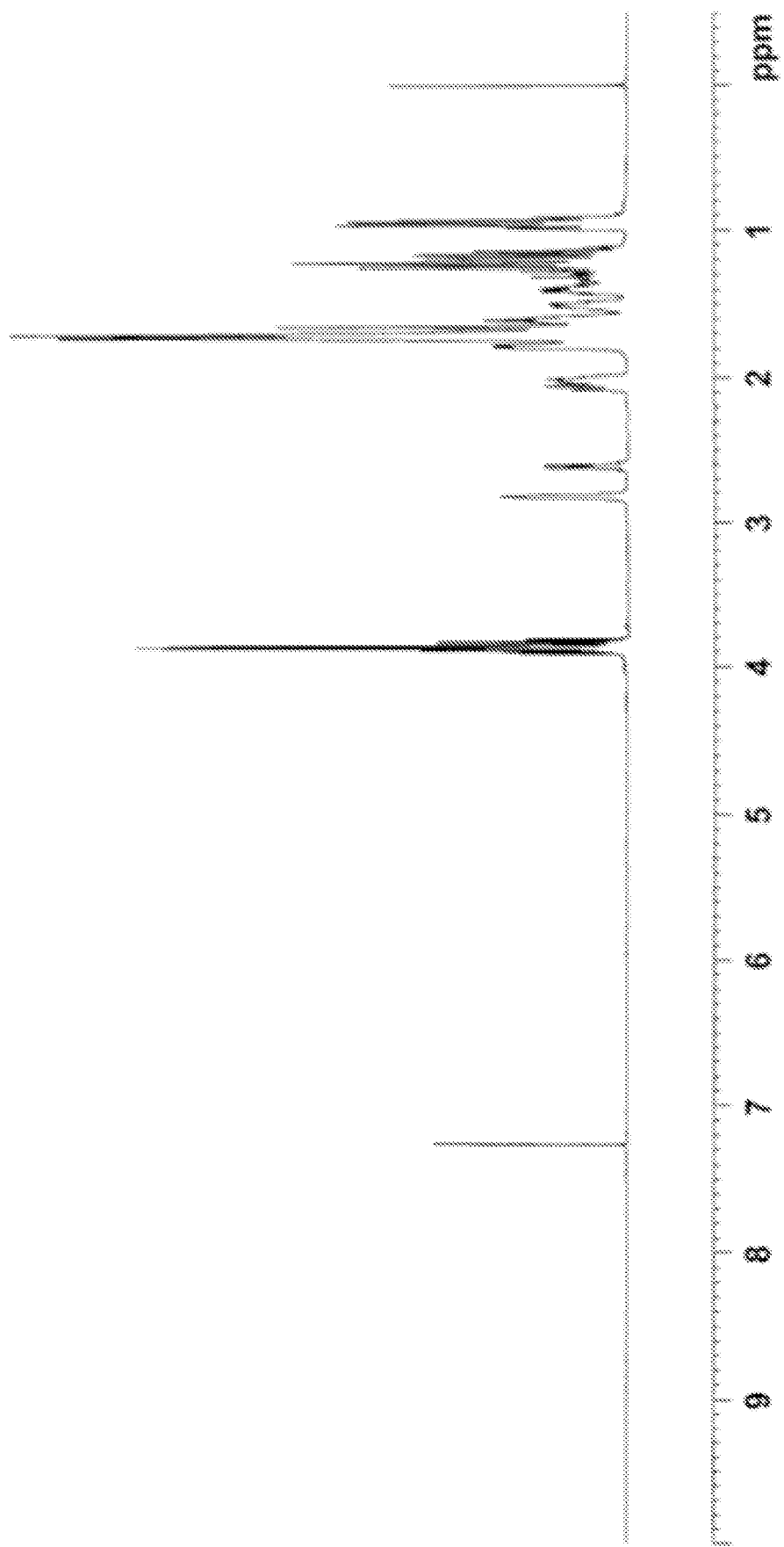
FIG. 2 shows the $^1$H-NMR spectrum of the di(cyclohexylmethyl) 1,2-cyclohexanedicarboxylate obtained in Example 1.
Figure 3:
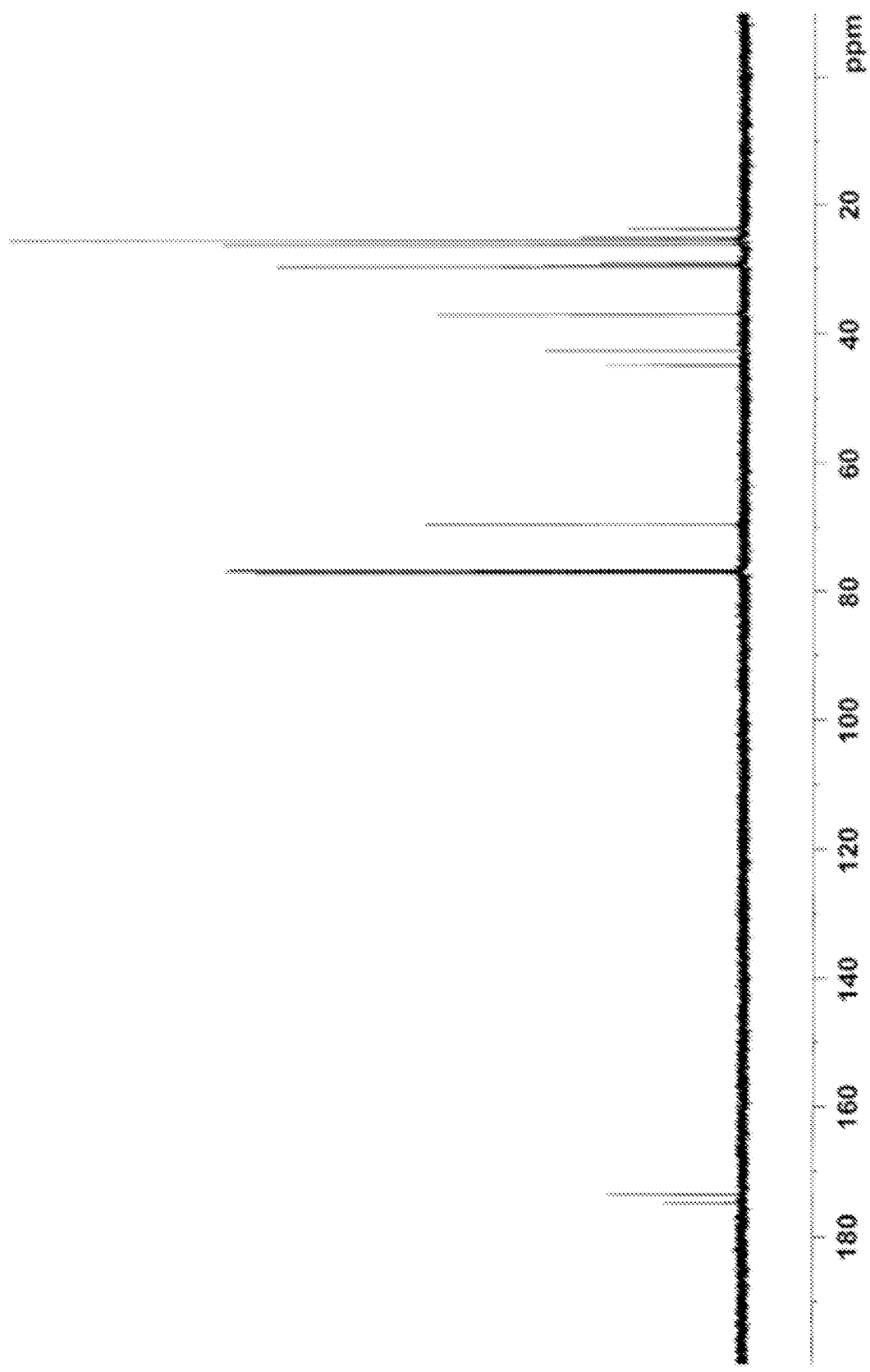
FIG. 3 shows the $^{13}$C-NMR spectrum of the di(cyclohexylmethyl) 1,2-cyclohexanedicarboxylate obtained in Example 1.

Further, the IR spectrum, $^1$H-NMR spectrum, and $^{13}$C-NMR spectrum of the di(cyclohexylmethyl) 1,2-cyclohexanedicarboxylate were measured. FIGS. 1 to 3 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform Example 2

985.4 g (2.51 mol) of di(4-methylcyclohexylmethyl) 1,2-cyclohexanedicarboxylate was obtained in the same manner as in Example 1, except that the cyclohexylmethanol was changed to 930.8 g (7.26 mol) of 4-methylcyclohexylmethanol. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (B). Table 1 shows the results.

Figure 4:
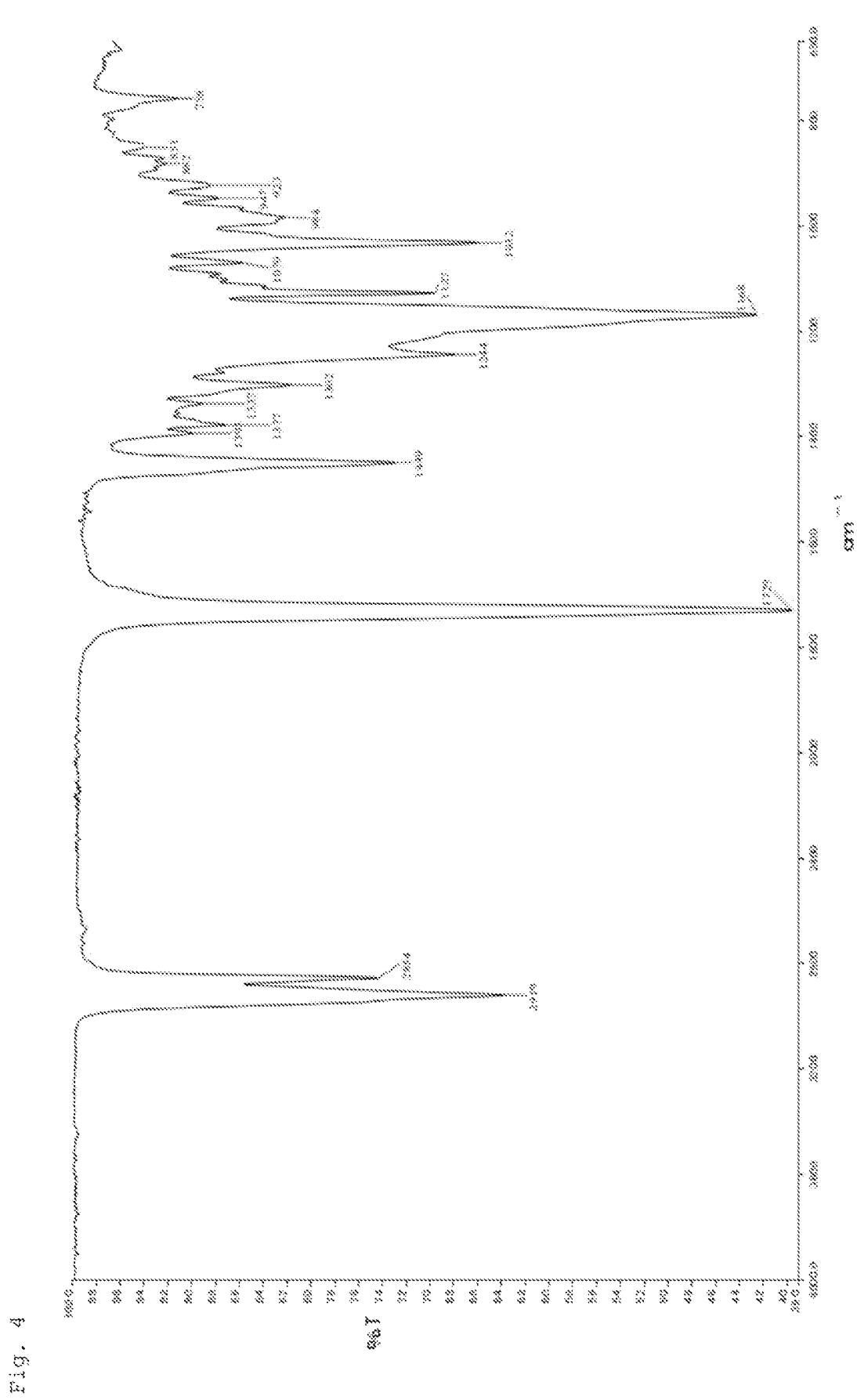
FIG. 4 shows the IR spectrum of the di(4-methylcyclohexylmethyl) 1,2-cyclohexanedicarboxylate obtained in Example 2.
Figure 5:
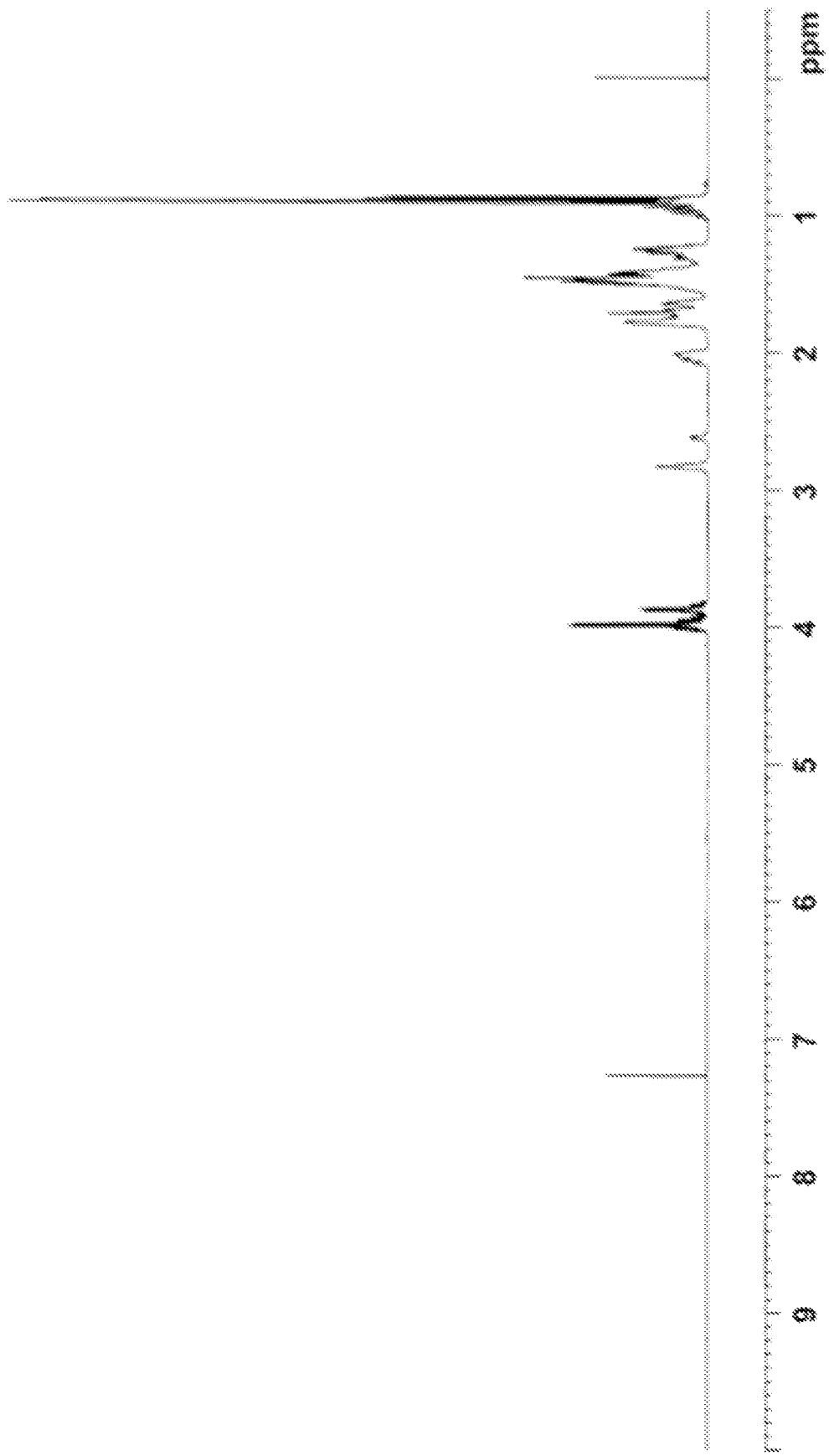
FIG. 5 shows the $^1$H-NMR spectrum of the di(4-zmethylcyclohexylmethyl) 1,2-cyclohexanedicarboxylate obtained in Example 2.
Figure 6:
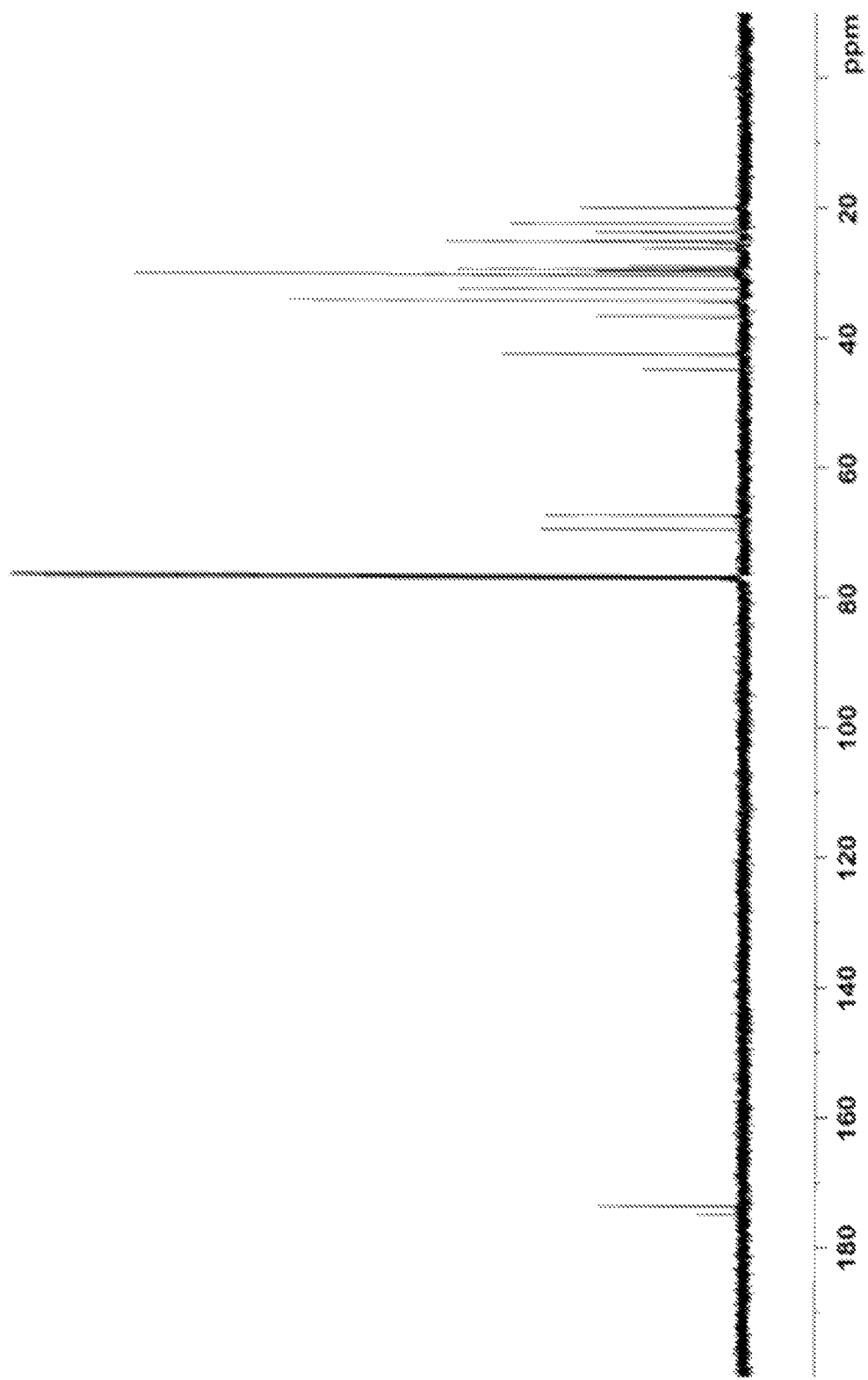
FIG. 6 shows the $^{13}$C-NMR spectrum of the di(4-methylcyclohexylmethyl) 1,2-cyclohexanedicarboxylate obtained in Example 2.

Further, the IR spectrum, $^1$H-NMR spectrum, and $^{13}$C-NMR spectrum of the di(4-methylcyclohexylmethyl) 1,2-cyclohexanedicarboxylate were measured. FIGS. 4 to 6 show the results. The peak of the $^1$H-NMR spectrum at around 7.27 ppm is a peak of the remaining proton of the solvent heavy chloroform. Moreover, the peak of the $^{23}$C-NMR spectrum at around 77 ppm is a peak of the solvent heavy chloroform.

Example 3

1027.2 g (2.44 mol) of di(3,4-dimethylcyclohexylmethyl) 1,2-cyclohexanedicarboxylate was obtained in the same manner as in Example 1, except that the cyclohexylmethanol was changed to 1032.7 g (7.26 mol) of 3,4-dimethylcyclohexylmethanol. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (C). Table 1 shows the results.

Figure 7:
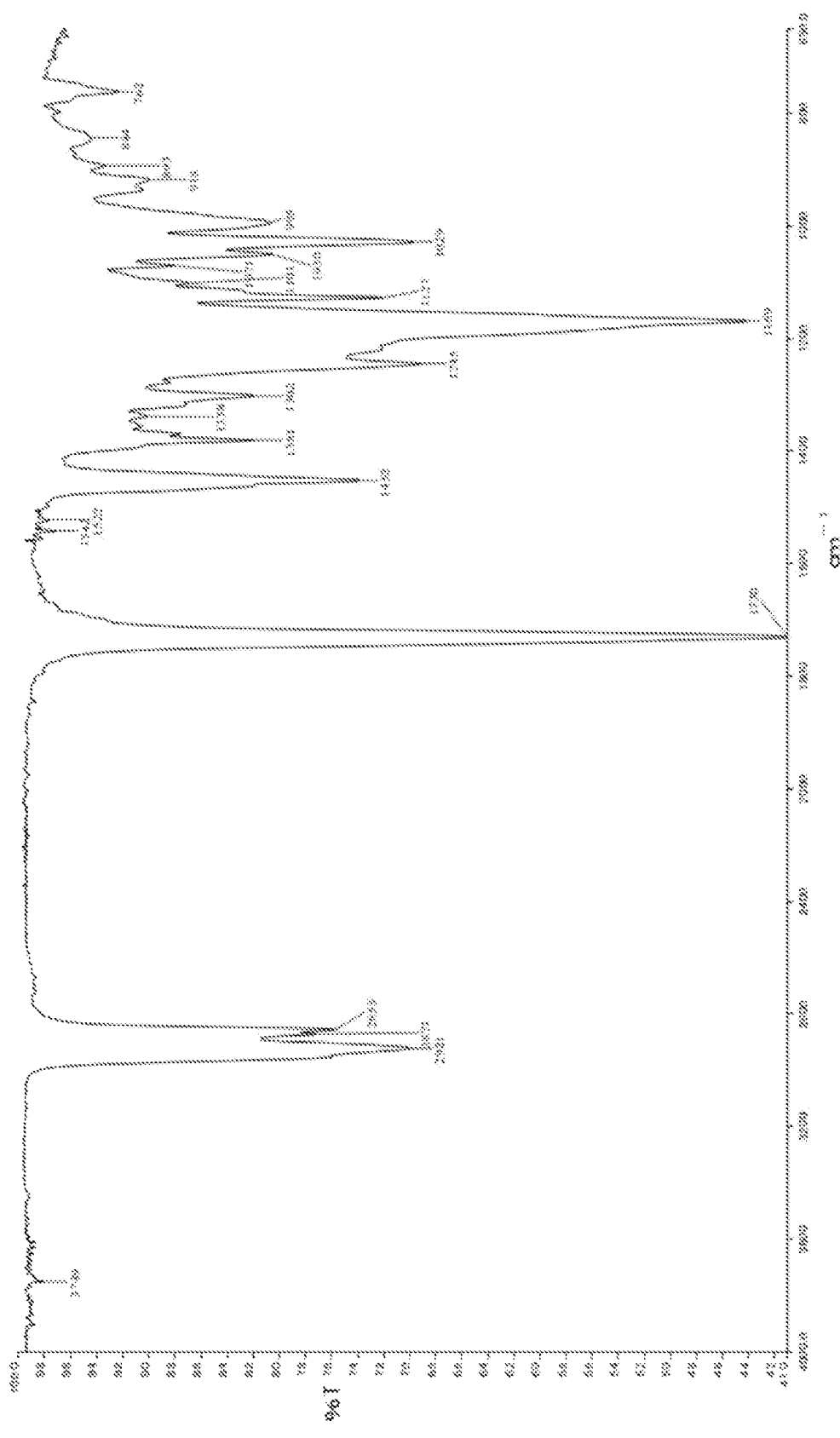
FIG. 7 shows the IR spectrum of the di(3,4-dimethylcyclohexylmethyl) 1,2-cyclohexanedicarboxylate obtained in Example 3.
Figure 8:
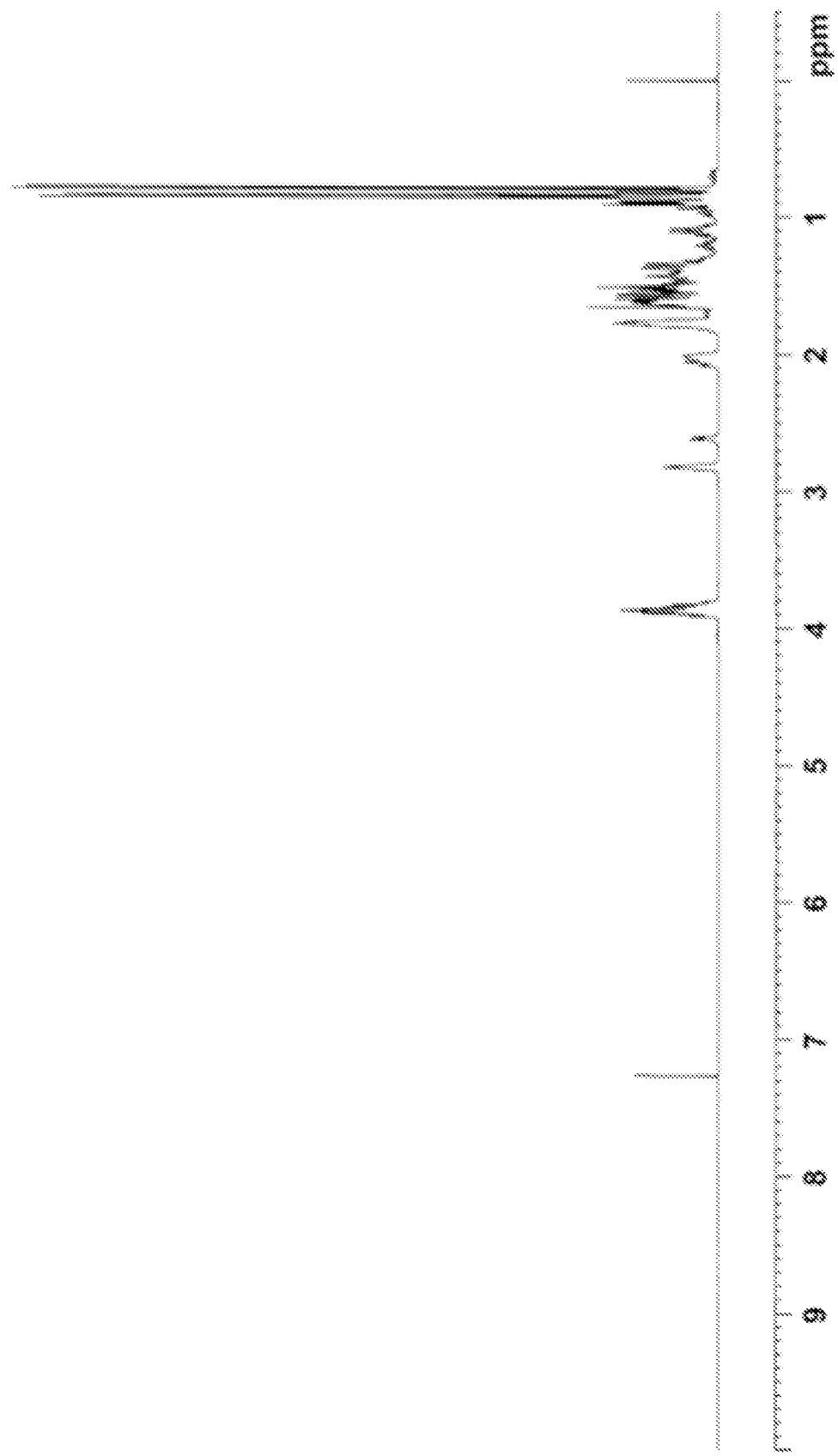
FIG. 8 shows the $^1$H-NMR spectrum of the di(3,4-dimethylcyclohexylmethyl) 1,2-cyclohexanedicarboxylate obtained in Example 3.
Figure 9:
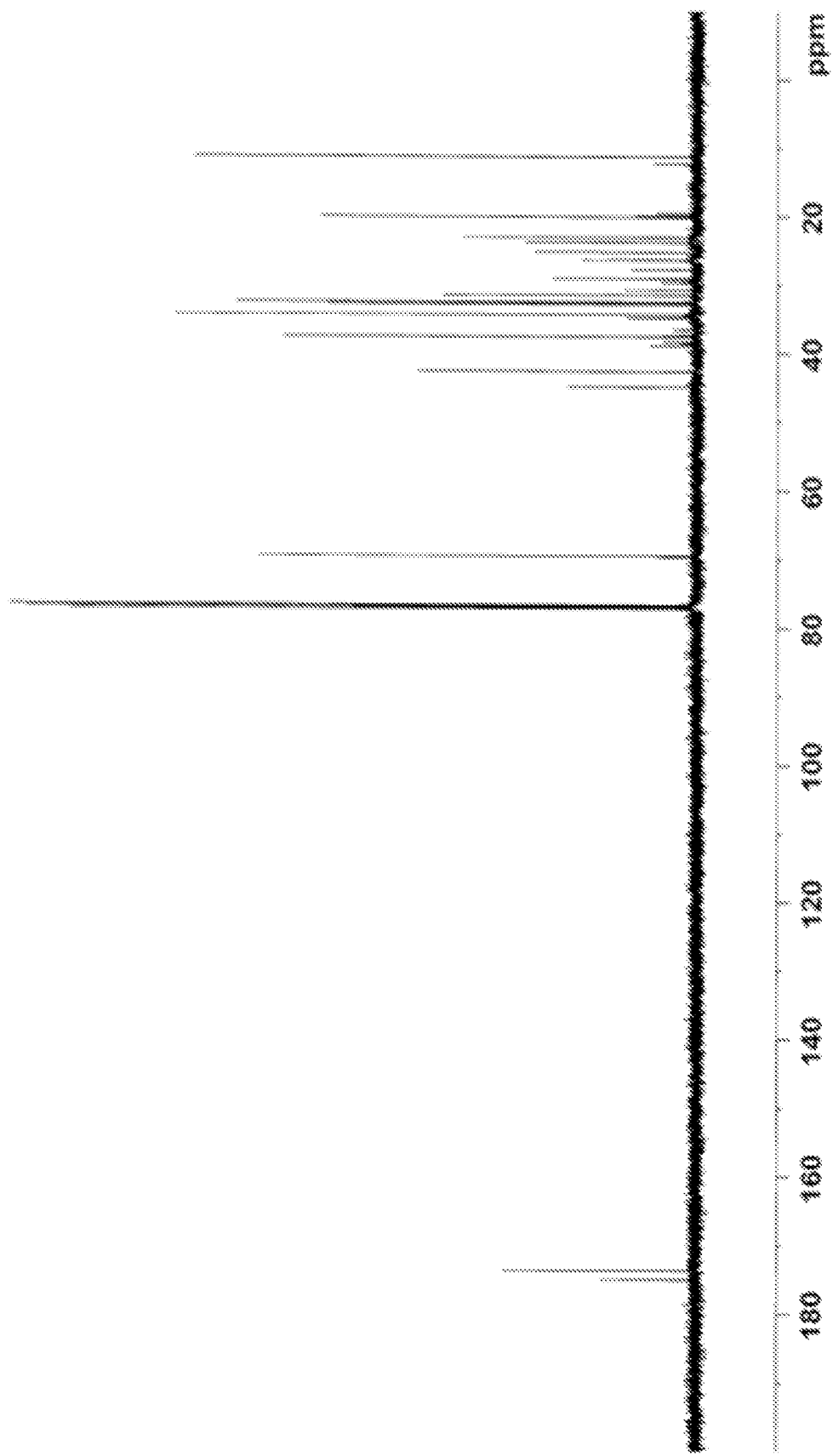
FIG. 9 shows the $^{13}$C-NMR spectrum of the di(3,4-dimethylcyclohexylmethyl) 1,2-cyclohexanedicarboxylate obtained in Example 3.

Further, the IR spectrum, $^1$H-NMR spectrum, and $^{13}$C-NMR spectrum of the di(3,4-dimethylcyclohexylmethyl) 1,2-cyclohexanedicarboxylate were measured. FIGS. 7 to 9 show the results. The peak of the $^1$H-NMR spectrum at around 7.27 ppm is a peak of the remaining proton of the solvent heavy chloroform. Moreover, the peak of the $^{23}$C-NMR spectrum at around 77 ppm is a peak of the solvent heavy chloroform.

Example 4

1147.0 g (3.03 mol) of di(cyclohexylmethyl) 4-methyl-1,2-cyclohexanedicarboxylate was obtained in the same manner as in Example 1, except that the 1,2-cyclohexanedicarboxylic anhydride was changed to 555.0 g (3.3 mol) of 4-methyl-1,2-cyclohexanedicarboxylic anhydride. The acid value of the obtained alicyclic dicarboxylic acid diester compound was 0.01 or less mg KOH/g, and the hydroxyl value was 1 mg KOH/g or less.

The physical properties were each evaluated using the alicyclic dicarboxylic acid diester compound as a lubricant base oil for power transmission (D). Table 1 shows the results.

Figure 10:
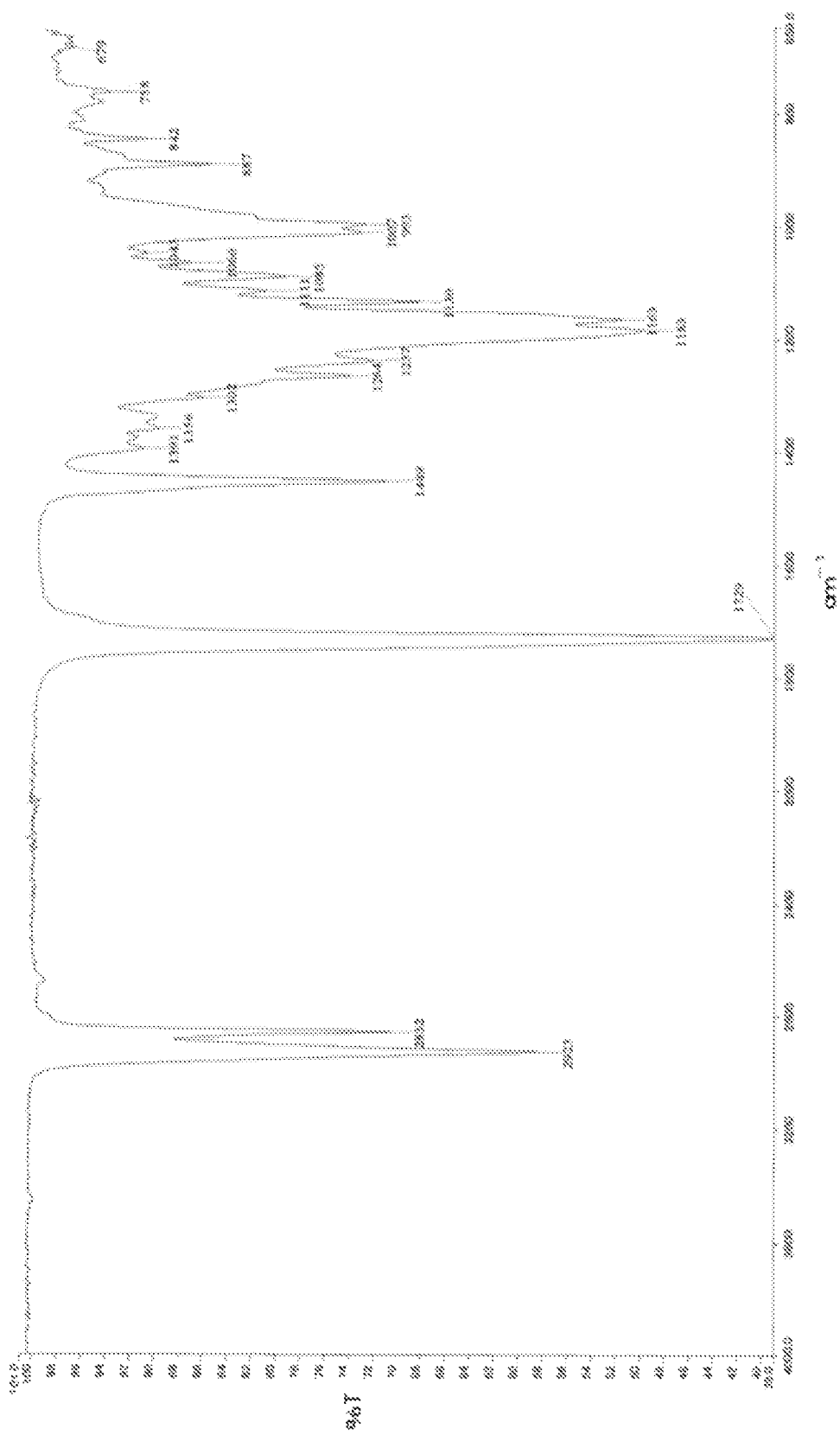
FIG. 10 shows the IR spectrum of the di(cyclohexylmethyl) 4-methyl-1,2-cyclohexanedicarboxylate obtained in Example 4.
Figure 11:
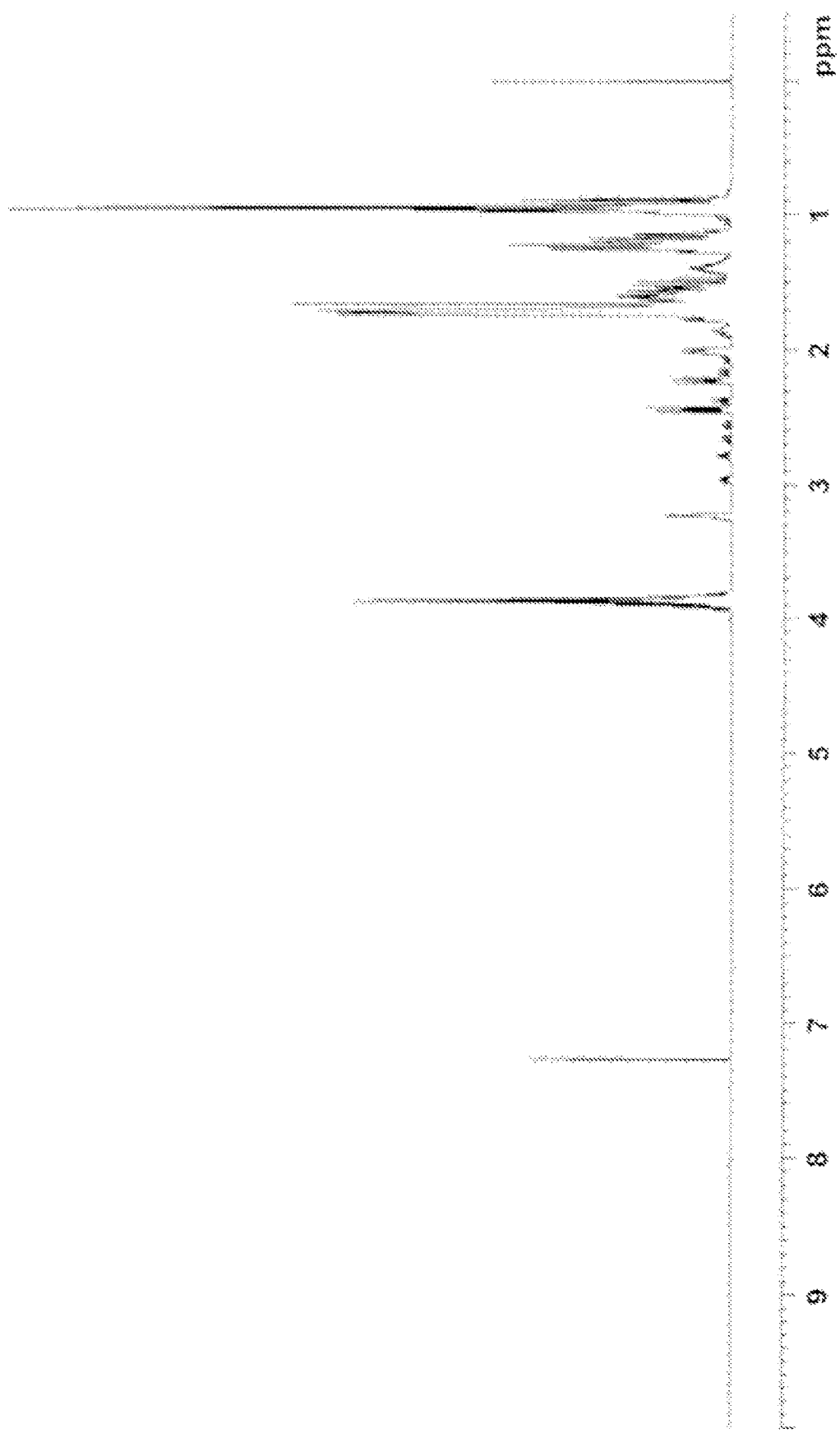
FIG. 11 shows the $^1$H-NMR spectrum of the di(cyclohexylmethyl) 4-methyl-1,2-cyclohexanedicarboxylate obtained in Example 4.

Further, the IR spectrum, $^1$H-NMR spectrum, and $^{13}$C-NMR spectrum of the di(cyclohexylmethyl) 4-methyl-1,2-cyclohexanedicarboxylate were measured. FIGS. 10 to 12 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Example 5

818.5 g (2.01 mol) of di(4-methylcyclohexylmethyl) 4-methyl-1,2-cyclohexanedicarboxylate was obtained in the same manner as in Example 2, except that the 1,2-cyclohexanedicarboxylic anhydride was changed to 555.0 g (3.3 mol) of 4-methyl-1,2-cyclohexanedicarboxylic anhydride. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (E). Table 1 shows the results.

Figure 13:
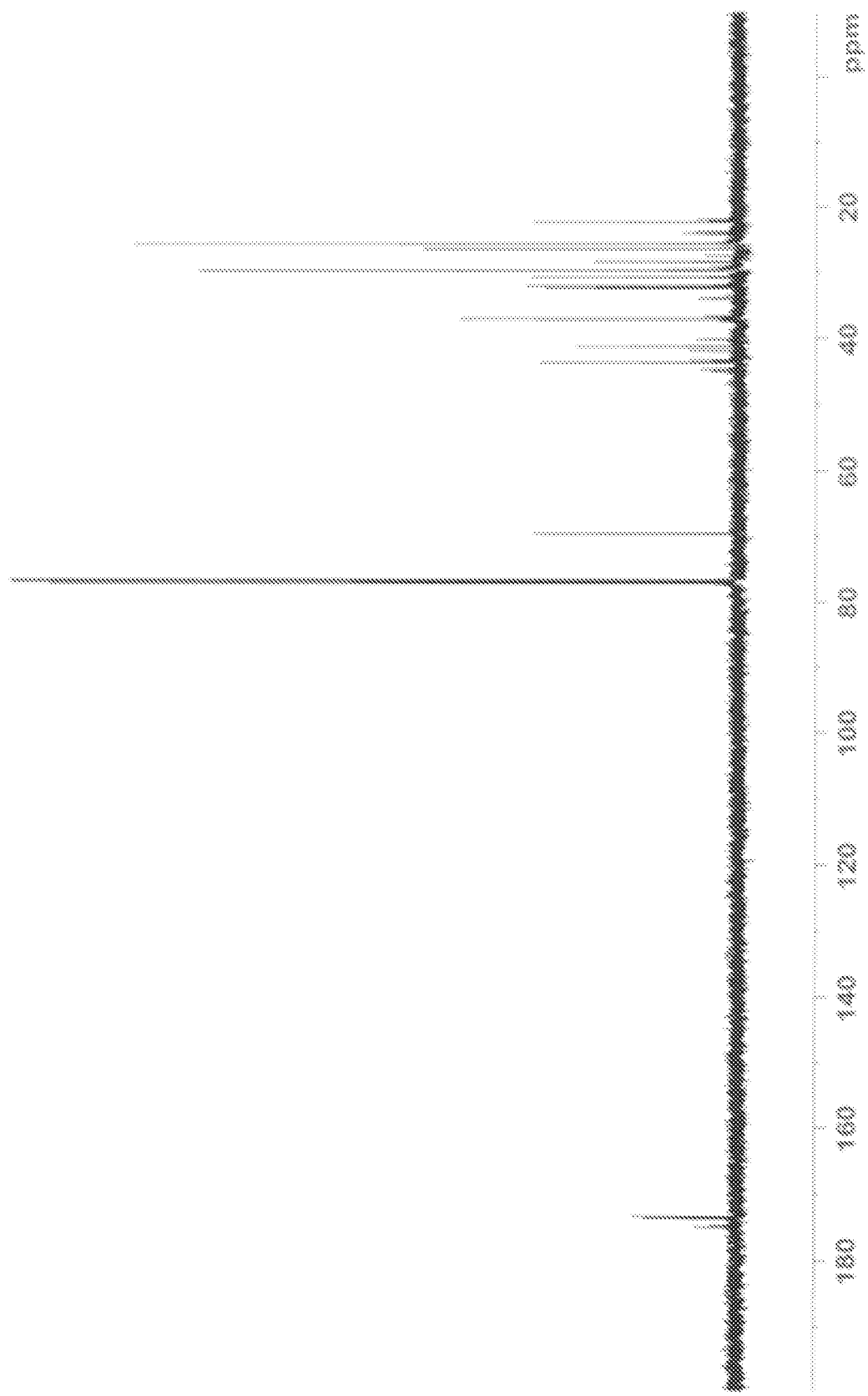
FIG. 13 shows the IR spectrum of di(4-methylcyclohexylmethyl) 4-methyl-1,2-cyclohexanedicarboxylate obtained in Example 5.
Figure 13:
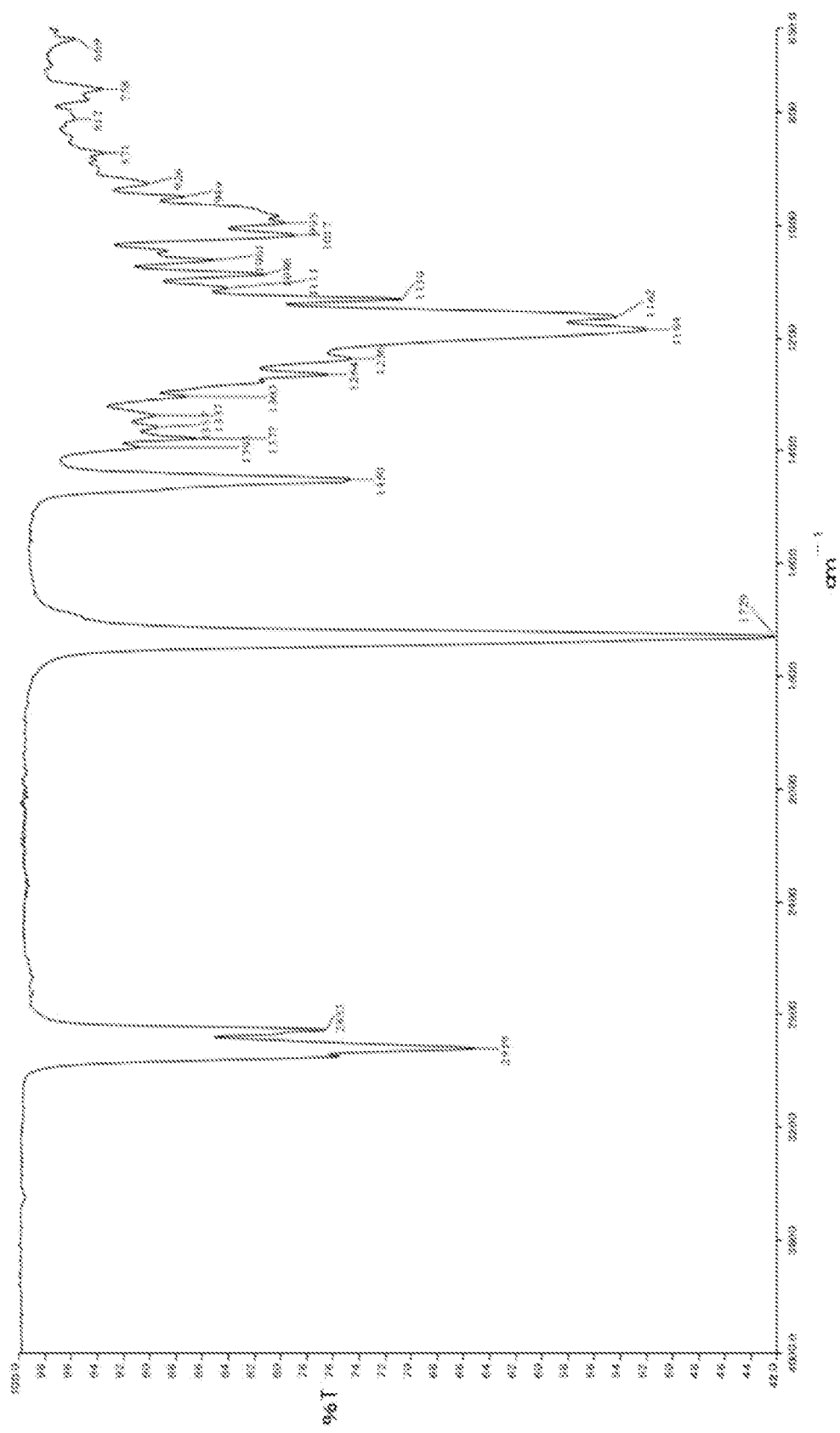
Figure 14:
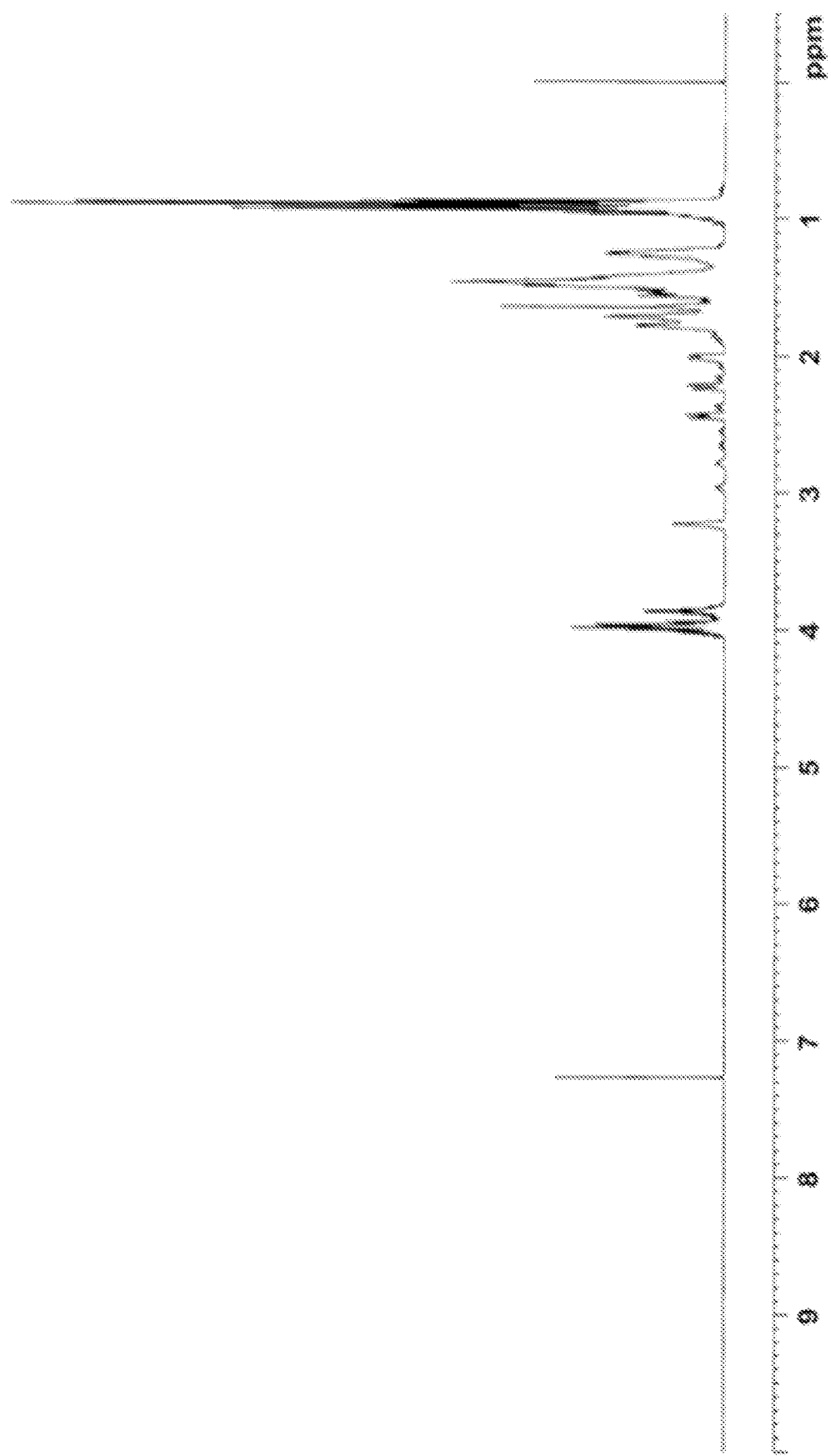
FIG. 14 shows the $^1$H-NMR spectrum of the di(4-methylcyclohexylmethyl) 4-methyl-1,2-cyclohexanedicarboxylate obtained in Example 5.
Figure 15:
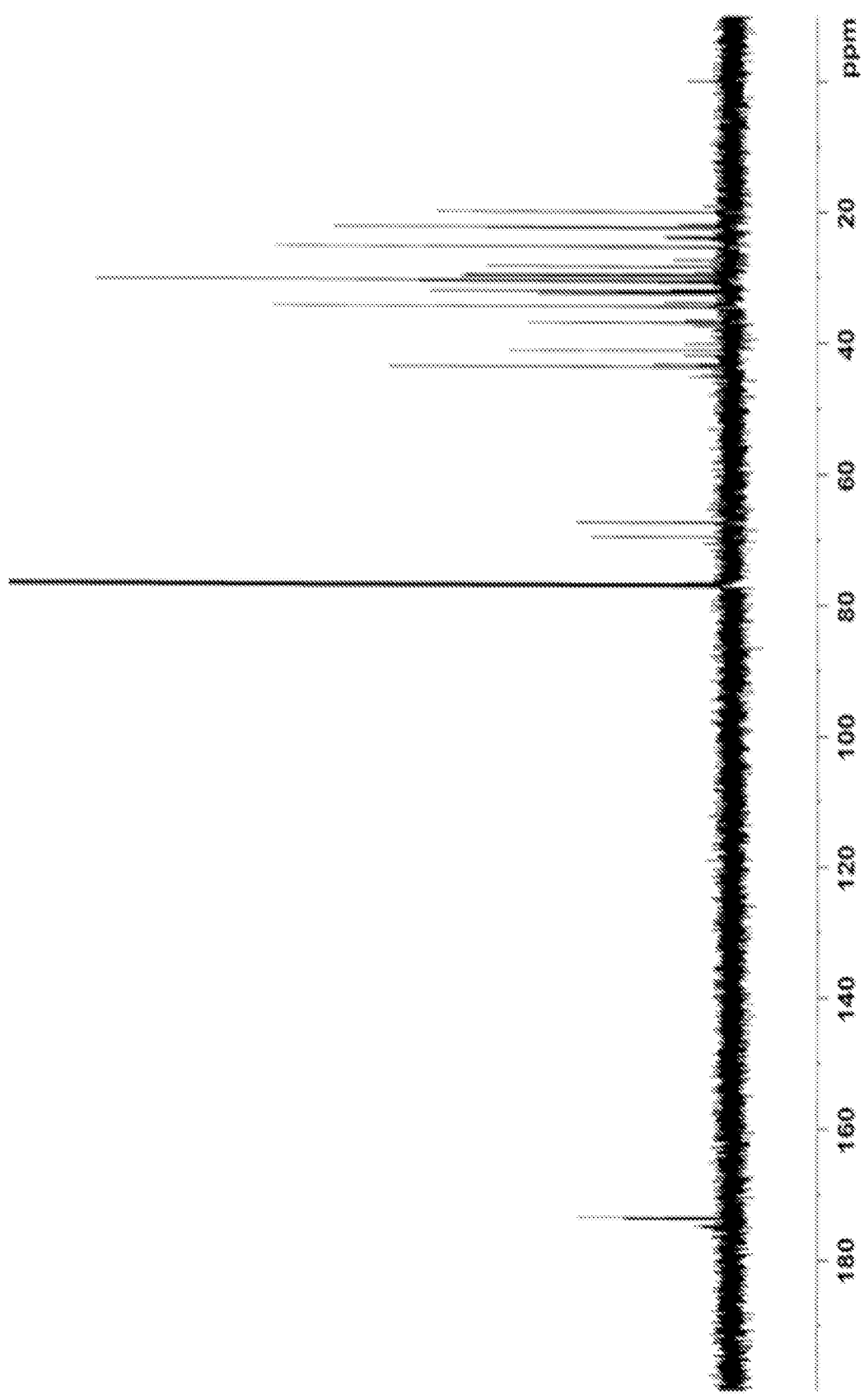
FIG. 15 shows the $^1$C-NMR spectrum of the di(4-methylcyclohexylmethyl) 4-methyl-1,2-cyclohexanedicarboxylate obtained in Example 5.

Further, the IR spectrum, $^1$H-NMR spectrum, and $^{13}$C-NMR spectrum of the di(4-methylcyclohexylmethyl) 4-methyl-1,2-cyclohexanedicarboxylate were measured. FIGS. 13 to 15 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Example 6

934.5 g (2.15 mol) of di(3,4-dimethylcyclohexylmethyl) 4-methyl-1,2-cyclohexanedicarboxylate was obtained in the same manner as in Example 3, except that the 1,2-cyclohexanedicarboxylic anhydride was changed to 555.0 g (3.3 mol) of 4-methyl-1,2-cyclohexanedicarboxylic anhydride. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (F). Table 1 shows the results.

Figure 16:
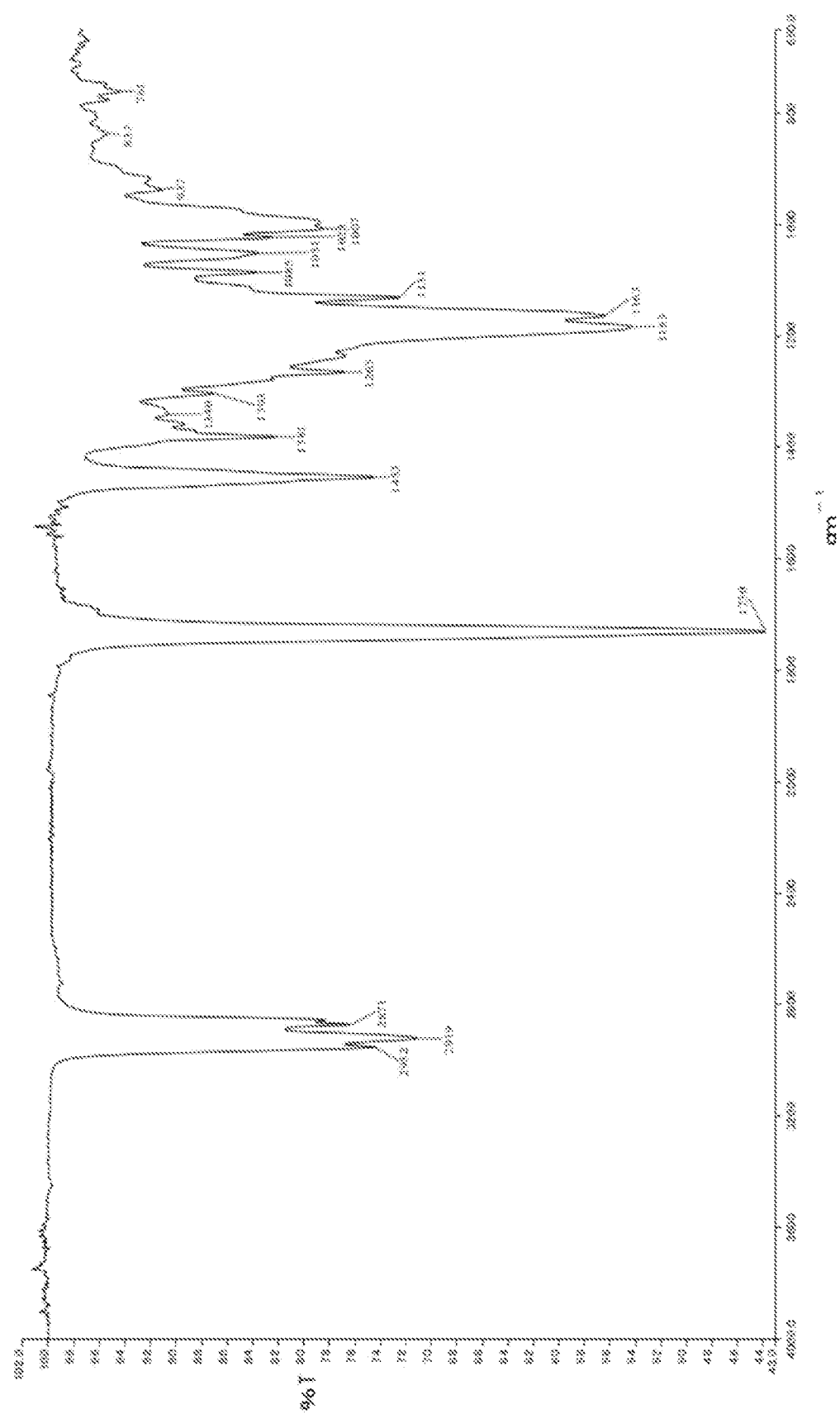
FIG. 16 shows the IR spectrum of the di(3,4-dimethylcyclohexylmethyl) 4-methyl-1,2-cyclohexanedicarboxylate obtained in Example 6.
Figure 17:
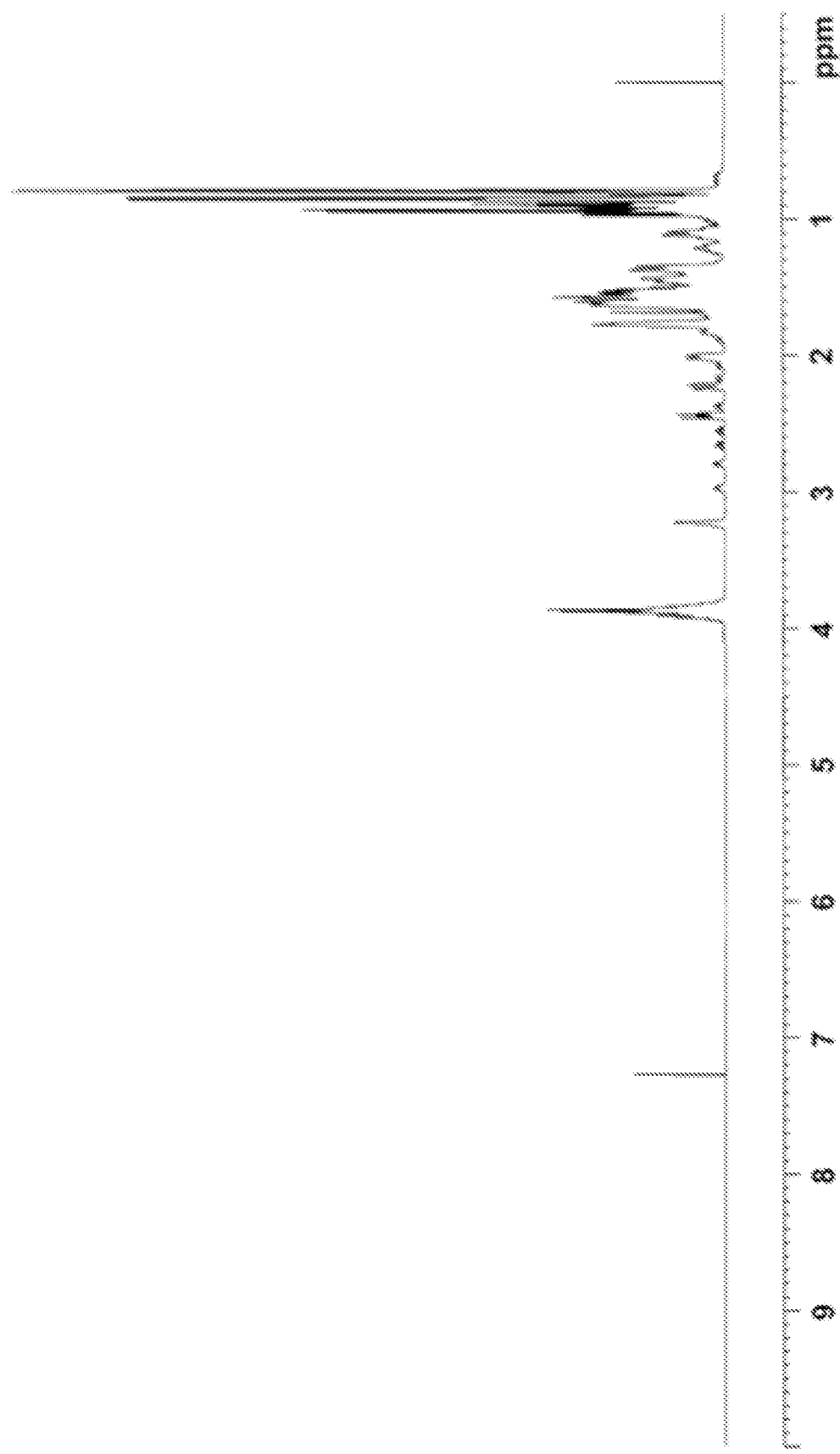
FIG. 17 shows the $^1$H-NMR spectrum of the di(3,4-dimethylcyclohexylmethyl) 4-methyl-1,2-cyclohexanedicarboxylate obtained in Example 6.
Figure 18:
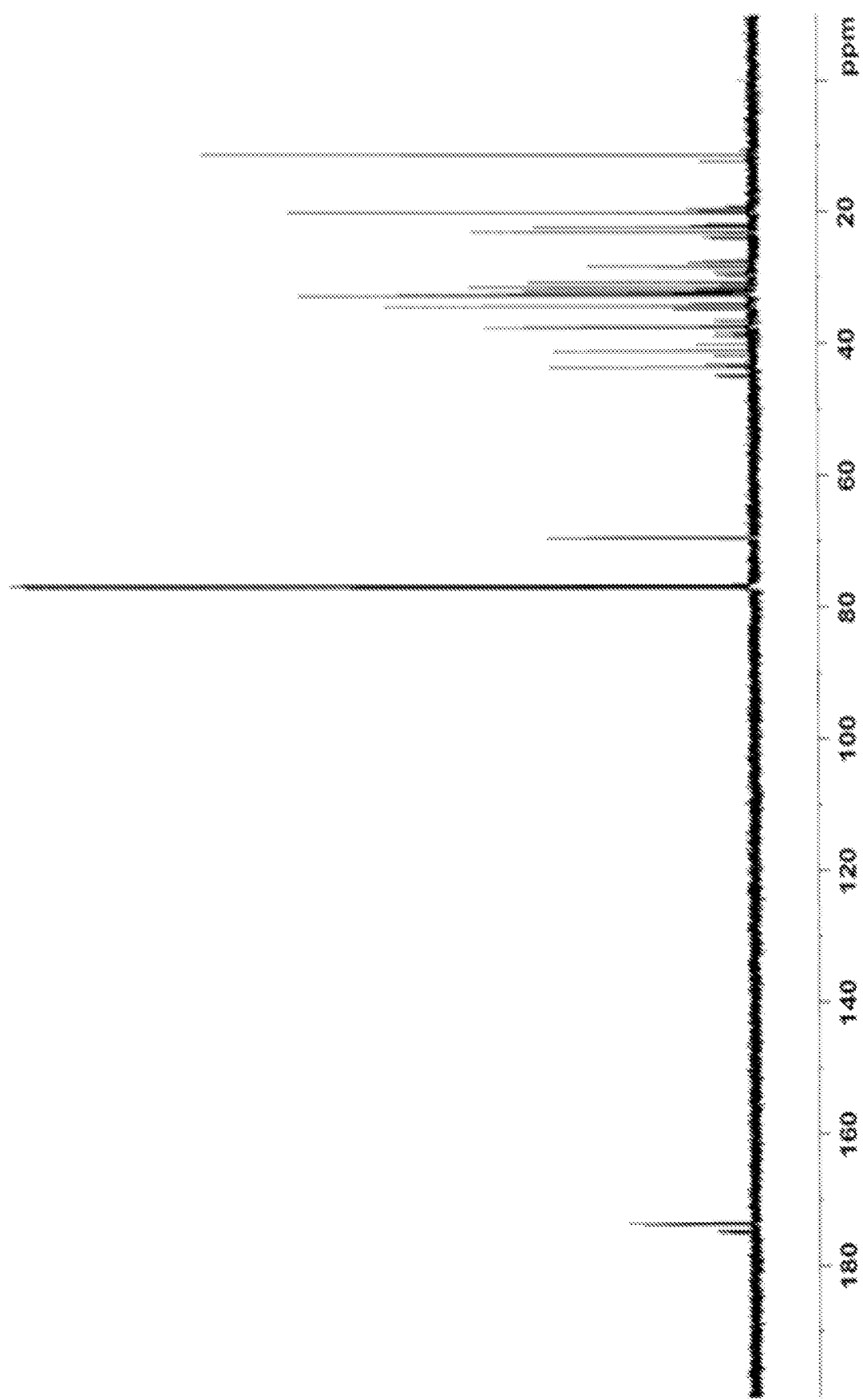
FIG. 18 shows the $^{13}$C-NMR spectrum of the di(3,4-dimethylcyclohexylmethyl) 4-methyl-1,2-cyclohexanedicarboxylate obtained in Example 6.

Further, the IR spectrum, $^1$H-NMR spectrum, and $^{13}$C-NMR spectrum of the di(3,4-dimethylcyclohexylmethyl) 4-methyl-1,2-cyclohexanedicarboxylate were measured. FIGS. 16 to 18 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Example 7

1083.8 g (2.80 mol) of a mixture of di(cyclohexylmethyl) methylbicyclo[2.2.1]heptane-2,3-dicarboxylate and di(cyclohexylmethyl) bicyclo[2.2.1]heptane-2,3-dicarboxylate was obtained in the same manner as in Example 1, except that the 1,2-cyclohexanedicarboxylic anhydride was changed to 580.8 g (3.3 mol) of a mixture of methylbicyclo [2.2.1]heptane-2,3-dicarboxylic anhydride and bicyclo [2.2.1]heptane-2,3-dicarboxylic anhydride. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (G). Table 1 shows the results.

Figure 19:
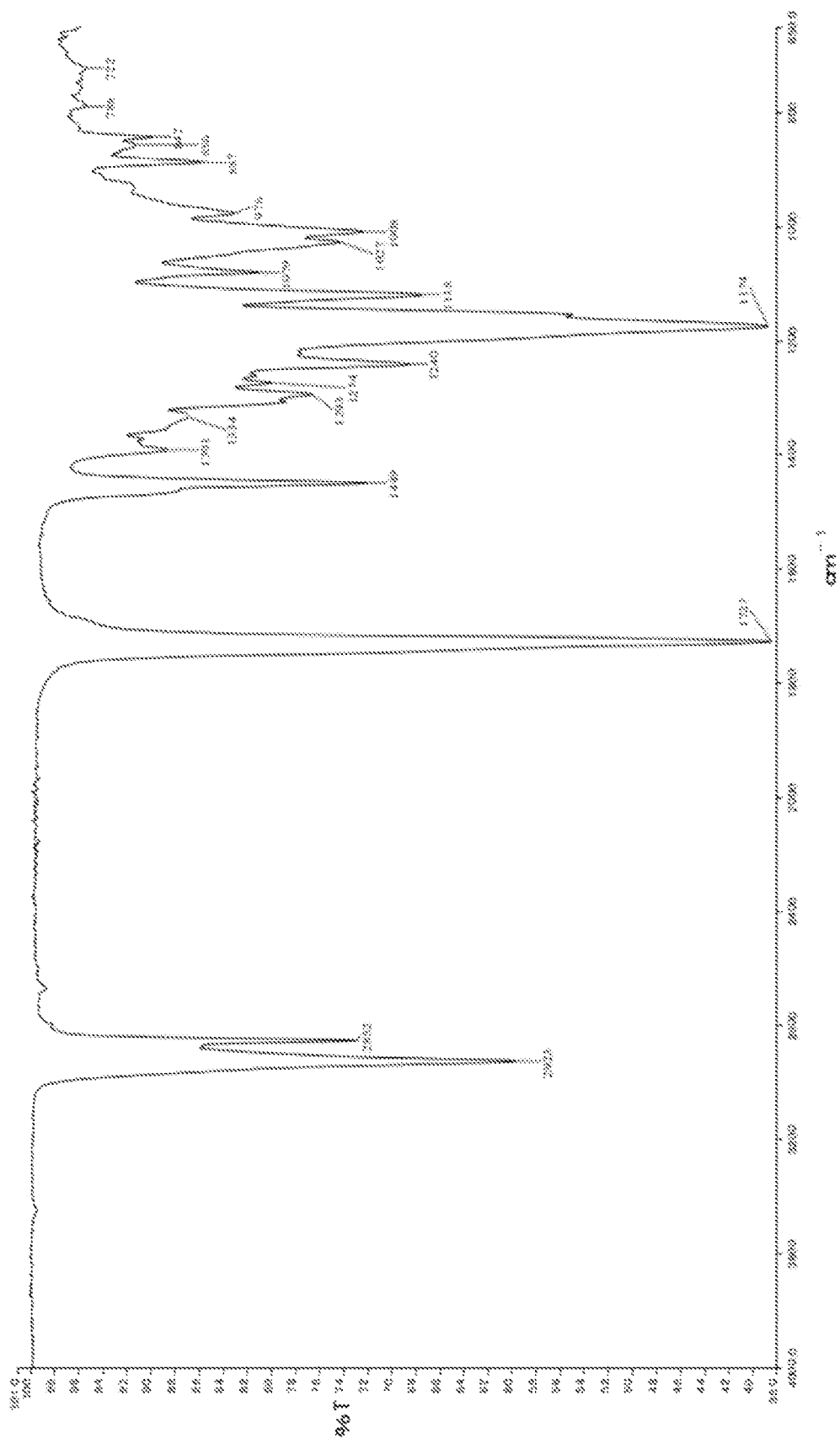
FIG. 19 shows the IR spectrum of the mixture of di(cyclohexylmethyl) methylbicyclo[2.2.1]heptane-2,3-dicarboxylate and di(cyclohexylmethyl) bicyclo[2.2.1]heptane-2,3-dicarboxylate obtained in Example 7.
Figure 20:
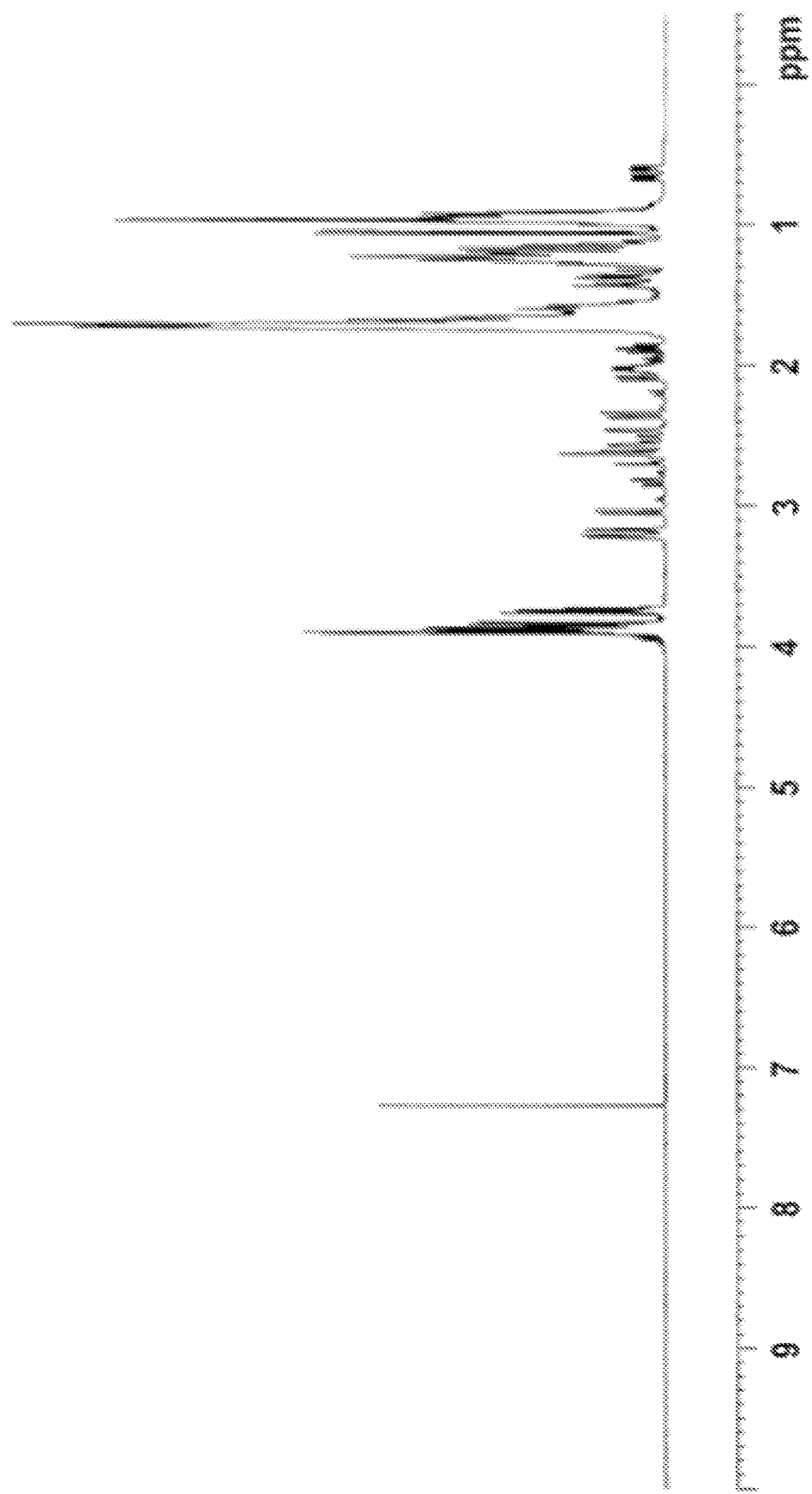
FIG. 20 shows the $^1$H-NMR spectrum of the mixture of di(cyclohexylmethyl) methylbicyclo[2.2.1]heptane-2,3-dicarboxylate and di(cyclohexylmethyl) bicyclo[2.2.1]heptane-2,3-dicarboxylate obtained in Example 7.
Figure 21:
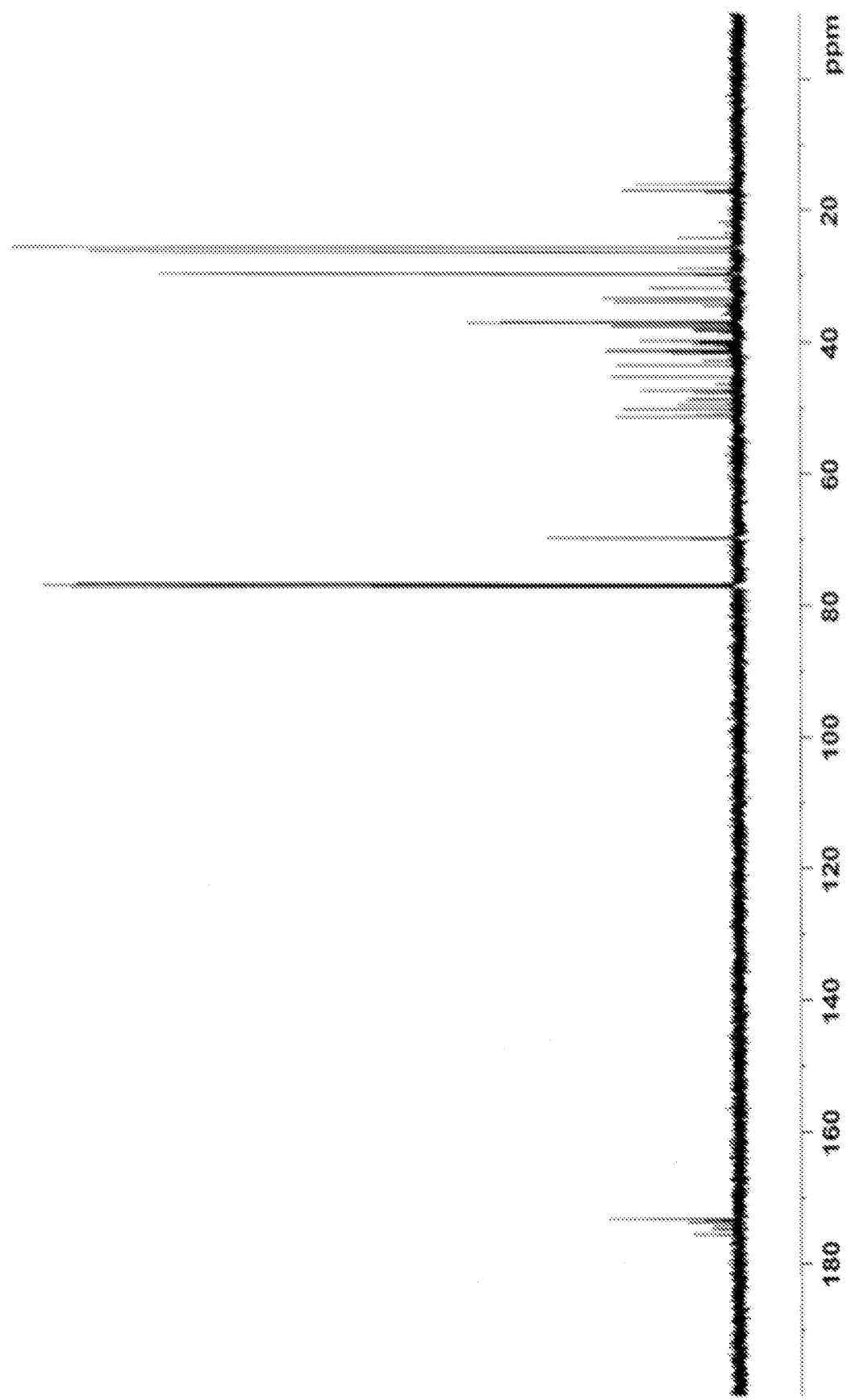
FIG. 21 shows the $^{13}$C-NMR spectrum of the mixture of di(cyclohexylmethyl) methylbicyclo[2.2.1]heptane-2,3-dicarboxylate and di(cyclohexylmethyl) bicyclo[2.2.1]heptane-2,3-dicarboxylate obtained in Example 7.

Further, the IR spectrum, $^1$H-NMR spectrum, and $^{13}$C-NMR spectrum of the alicyclic dicarboxylic acid diester compound were measured. FIGS. 19 to 21 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Example 8

1025.8 g (2.48 mol) of a mixture of di(4-methylcyclohexylmethyl) methylbicyclo[2.2.1]heptane-2,3-dicarboxylate and di(4-methylcyclohexylmethyl) bicyclo[2.2.1]heptane-2,3-dicarboxylate was obtained in the same manner as in Example 7, except that the cyclohexylmethanol was changed to 930.8 g (7.26 mol) of 4-methylcyclohexylmethanol. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (H). Table 1 shows the results.

Figure 22:
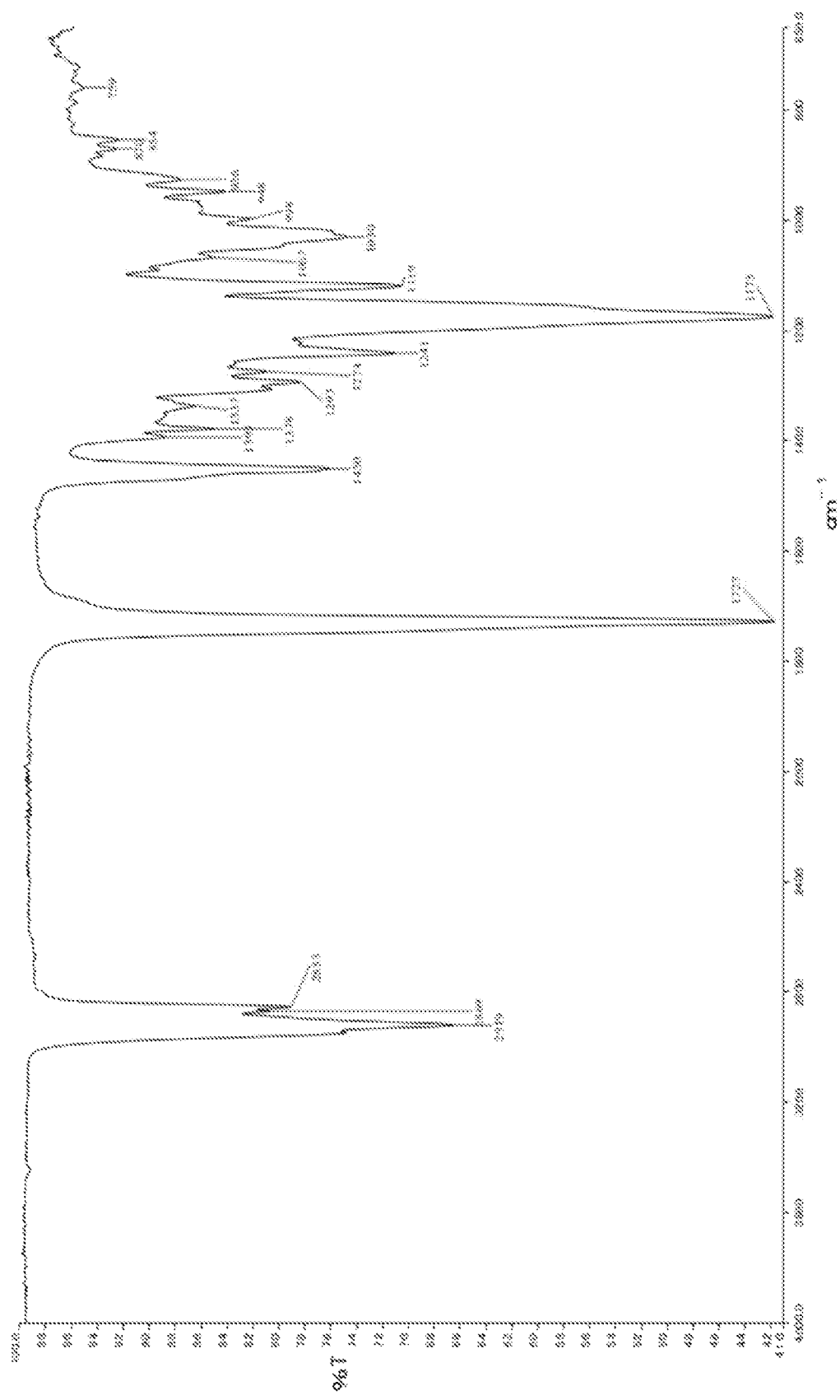
FIG. 22 shows the IR spectrum of the mixture of di(4-methylcyclohexylmethyl) methylbicyclo[2.2.1]heptane-2,3-dicarboxylate and di(4-methylcyclohexylmethyl) bicyclo[2.2.1]heptane-2,3-dicarboxylate obtained in Example 8.
Figure 23:
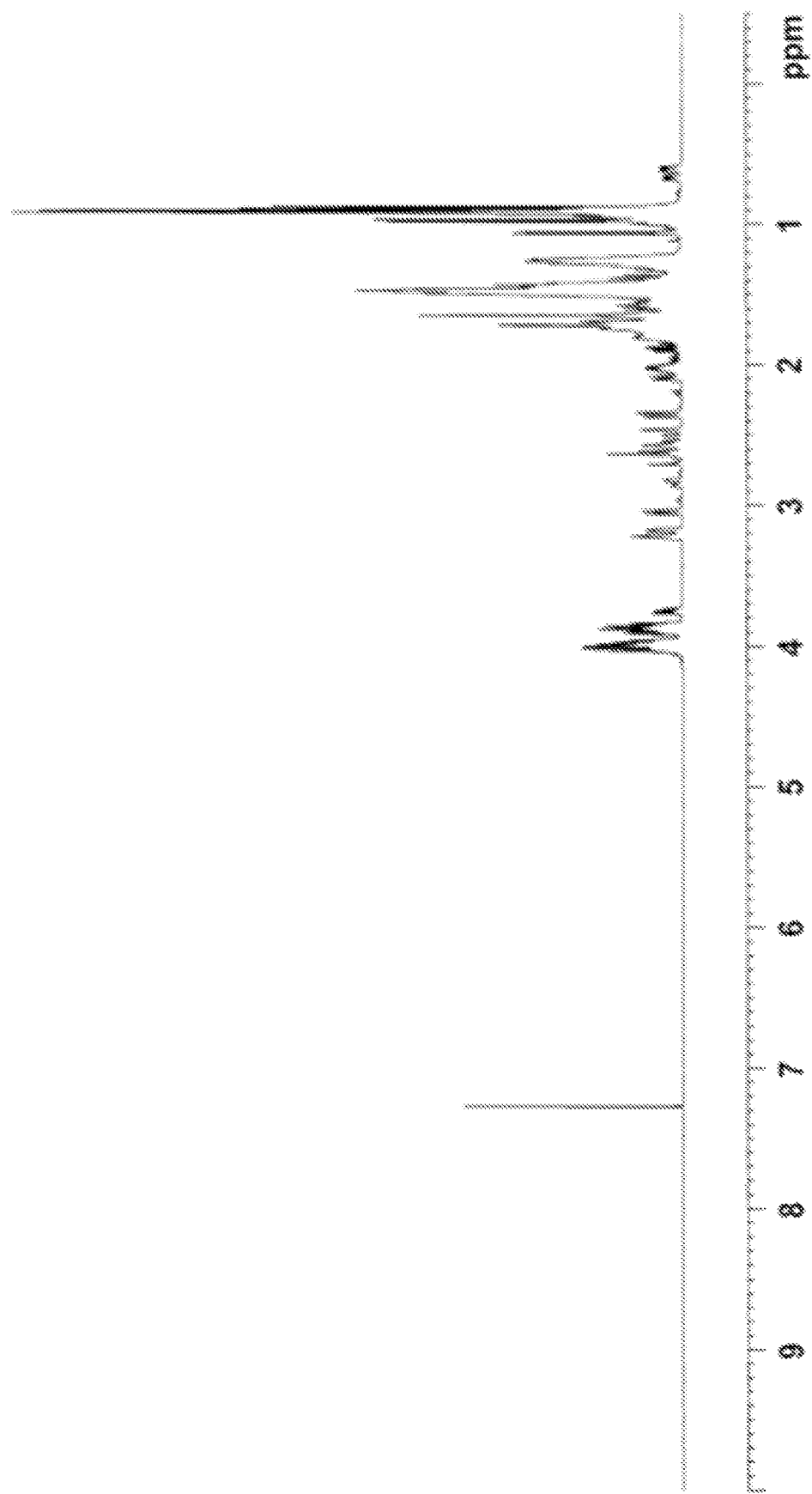
FIG. 23 shows the $^1$H-NMR spectrum of the mixture of di(4-methylcyclohexylmethyl) methylbicyclo[2.2.1]heptane-2,3-dicarboxylate and di(4-methylcyclohexylmethyl) bicyclo[2.2.1]heptane-2,3-dicarboxylate obtained in Example 8.
Figure 24:
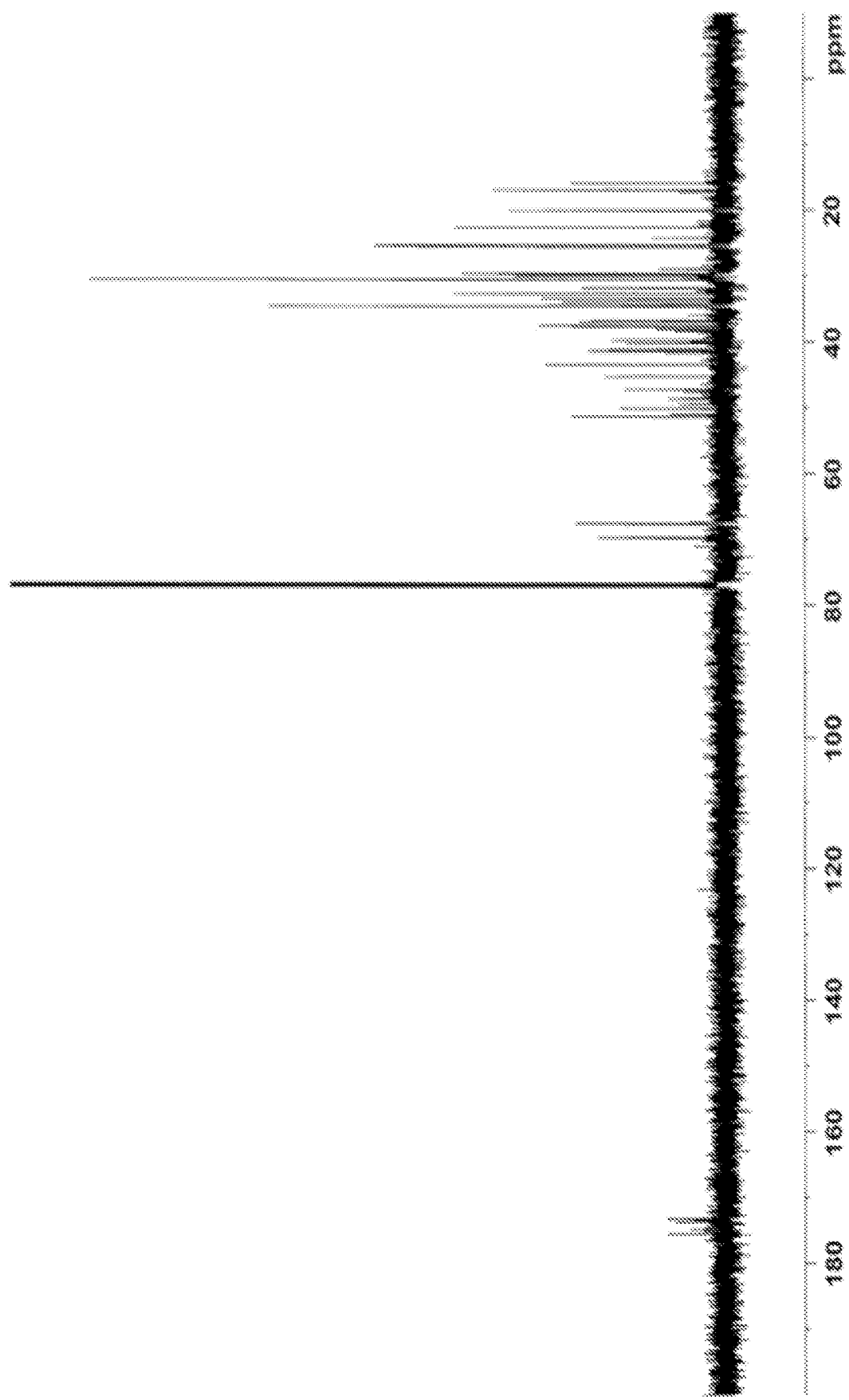
FIG. 24 shows the $^{13}$C-NMR spectrum of the mixture of di(4-methylcyclohexylmethyl) methylbicyclo[2.2.1]heptane-2,3-dicarboxylate and di(4-methylcyclohexylmethyl) bicyclo[2.2.1]heptane-2,3-dicarboxylate obtained in Example 8.

Further, the IR spectrum, $^1$H-NMR spectrum, and $^{13}$C-NMR spectrum of the alicyclic dicarboxylic acid diester compound were measured. FIGS. 22 to 24 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Example 9

1095.2 g (2.47 mol) of a mixture of di(3,4-dimethylcyclohexylmethyl) methylbicyclo[2.2.1]heptane-2,3-dicarboxylate and di(3,4-dimethylcyclohexylmethyl) bicyclo [2.2.1]heptane-2,3-dicarboxylate was obtained in the same manner as in Example 7, except that the cyclohexylmethanol was changed to 1032.7 g (7.26 mol) of 3,4-dimethylcyclohexylmethanol. The acid value of the obtained alicyclic dicarboxylic acid diester compound was 0.01 mg KOH/g or less, and the hydroxyl value was 1 mg KOH/g or less.

The physical properties were each evaluated using the alicyclic dicarboxylic acid diester compound as a lubricant base oil for power transmission (I). Table 1 shows the results.

Figure 25:
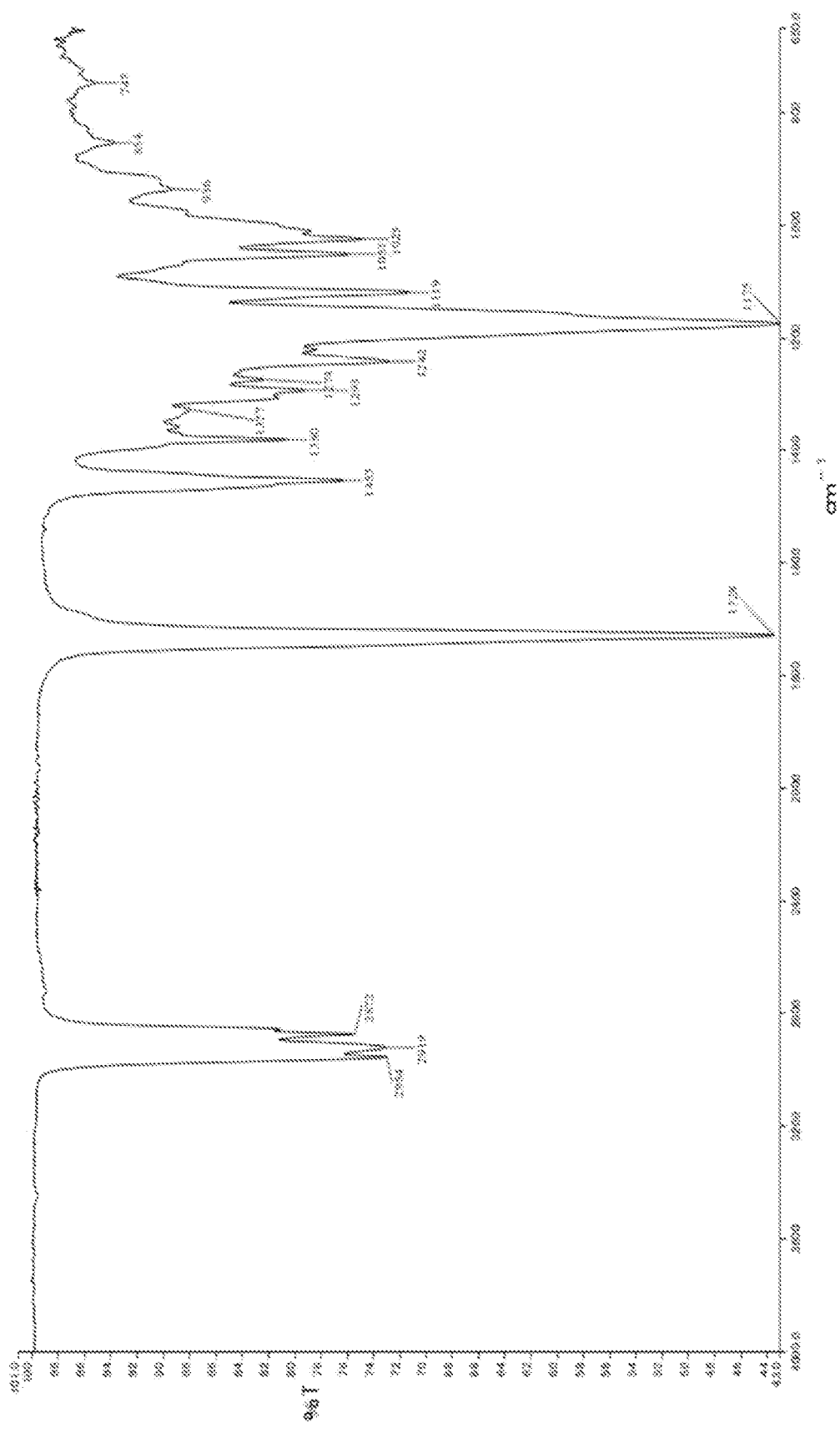
FIG. 25 shows the IR spectrum of the mixture of di(3,4-dimethylcyclohexylmethyl) methylbicyclo[2.2.1]heptane-2,3-dicarboxylate and di(3,4-dimethylcyclohexylmethyl) bicyclo[2.2.1]heptane-2,3-dicarboxylate obtained in Example 9.
Figure 26:
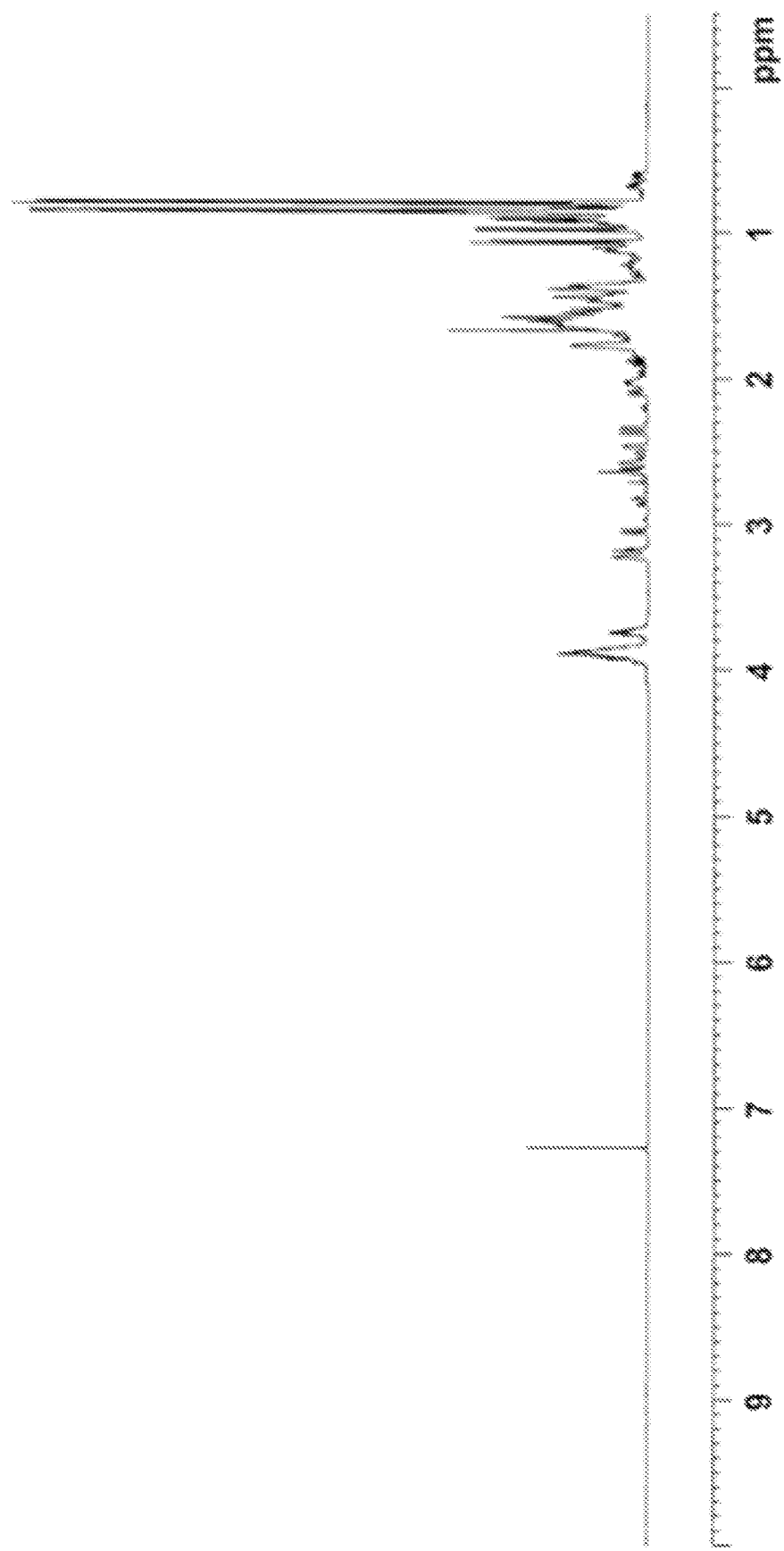
FIG. 26 shows the $^1$H-NMR spectrum of the mixture of di(3,4-dimethylcyclohexylmethyl) methylbicyclo[2.2.1]

Further, the IR spectrum, $^1$H-NMR spectrum, and $^{13}$C-NMR spectrum of the alicyclic dicarboxylic acid diester compound were measured. FIGS. 25 to 27 show the results. The peak of the $^1$H-NMR spectrum at around 7.27 ppm is a peak of the remaining proton of the solvent heavy chloroform. Moreover, the peak of the $^{13}$C-NMR spectrum at around 77 ppm is a peak of the solvent heavy chloroform.

Comparative Example 1

1189.8 g (3.00 mol) of di(2-ethylhexyl) 1,2-cyclohexanedicarboxylate was obtained in the same manner as in Example 1, except that the cyclohexylmethanol was changed to 945.5 g (7.26 mol) of 2-ethylhexanol. The acid value of the obtained alicyclic dicarboxylic acid diester, which was not the present invention, was 0.01 mg KOH/g or less, and the hydroxyl value was 1 mg KOH/g or less.

The physical properties were each evaluated using the alicyclic dicarboxylic acid diester as a lubricant base oil for power transmission (a). Table 2 shows the results.

Comparative Example 2

1201.2 g (3.03 mol) of di(n-octyl) 1,2-cyclohexanedicarboxylate was obtained in the same manner as in Example 1, except that the cyclohexylmethanol was changed to 945.5 g (7.26 mol) of n-octanol. The acid value of the obtained alicyclic dicarboxylic acid diester, which was not the present invention, was 0.01 mg KOH/g or less, and the hydroxyl value was 1 mg KOH/g or less.

The physical properties were each evaluated using the alicyclic dicarboxylic acid diester as a lubricant base oil for power transmission (b). Table 2 shows the results.

Comparative Example 3

The physical properties were each evaluated using diisodecyl adipate as a lubricant base oil for power transmission (c). Table 2 shows the results.

Comparative Example 4

The physical properties were each evaluated using mineral oil Y as a lubricant base oil for power transmission (d). Table 2 shows the results.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| Diester | Dicarboxylic anhydride | HH | HH | HH | MH | MH | MH | HNA | HNA | HNA |
| | Alcohol | CHM | 4-MCHM | 3,4-DMCHM | CHM | 4-MCHM | 3,4-DMCHM | CHM | 4-MCHM | 3,4-DMCHM |
| Lubricant base oil for power transmission | | (A) | (B) | (C) | (D) | (E) | (F) | (G) | (H) | (I) |
| Traction coefficient (60° C.) | | 0.105 | 0.110 | 0.110 | 0.117 | 0.108 | 0.114 | 0.112 | 0.101 | 0.107 |
| Kinetic viscosity | 100° C. | 8.78 | 9.15 | 12.61 | 9.12 | 9.71 | 13.27 | 13.42 | 13.61 | 19.13 |
| (mm$^2$/s) | 40° C. | 130.3 | 141.7 | 299.3 | 148.8 | 167.6 | 348.4 | 353.7 | 359.4 | 792.1 |
| Pour point (° C.) | | −15 | −17.5 | −12.5 | −20 | −10 | −7.5 | −5 | 0 | 2.5 |
| Flash point (° C.) | | 222 | 243 | 250 | 226 | 238 | 744 | 233 | 242 | 246 |

TABLE 2

|  |  | Comparative Example 1 | Comparative Example 2 | Comparative Example 3 | Comparative Example 4 |
|---|---|---|---|---|---|
| Diester | Dicarboxylic anhydride | HH | HH | DIDA | YUBASE |
|  | Alcohol | 2EH | nC8 |  |  |
| Lubricant base oil for power transmission |  | (a) | (b) | (c) | (d) |
| Traction coefficient (60° C.) |  | 0.053 | 0.042 | 0.035 | 0.053 |
| Kinetic viscosity (mm²/s) | 100° C. | 3.41 | 3.14 | 3.50 | 3.05 |
|  | 40° C. | 18.00 | 13.04 | 14.50 | 12.25 |
| Pour point (° C.) |  | −52.5 | −50.0 | −63.0 | −35.0 |
| Flash point (° C.) |  | 214 | 210 | 235 | 190 |

As is clear from Table 1, the lubricant base oils for power transmission shown in Examples 1 to 9 have a traction coefficient as high as 0.1 or more and a flash point as high as 215° C. or more.

In contrast, the base oils of Comparative Examples 1 to 4 have a traction coefficient as low as less than 0.06.

In light of the above, the use of the alicyclic dicarboxylic acid diester compounds of the present invention results in base oils that realize a high traction coefficient and that also have a high flash point. The alicyclic dicarboxylic acid diester compounds of the present invention can be suitably used as lubricant base oils for power transmission (particularly lubricant base oils for traction drives).

INDUSTRIAL APPLICABILITY

The lubricant base oil for power transmission of the present invention has a high traction coefficient and a high flash point, and thus can be suitably used as a lubricant base oil for power transmission (particularly a lubricant base oil for traction drives) for vehicles, marine vessels, aircraft, precision equipment, etc.

The invention claimed is:

1. A lubricant base oil for power transmission comprising an alicyclic dicarboxylic acid diester compound represented by general formula (1):

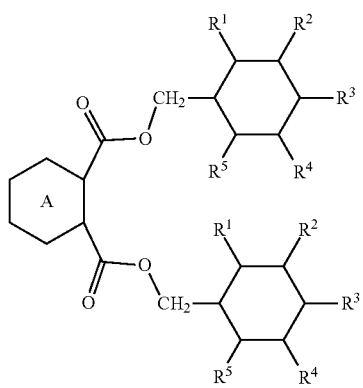

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; and ring A is

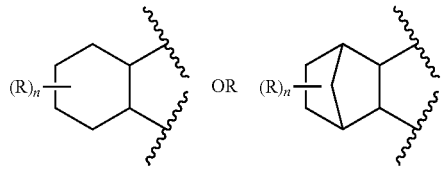

wherein R represents $C_{1-3}$ alkyl, and n represents 0, 1, or 2; when n represents 2, R may be the same or different.

2. The lubricant base oil for power transmission according to claim 1, wherein $R^1$ and $R^5$ are hydrogen.

3. The lubricant base oil for power transmission according to claim 1, wherein $R^1$, $R^2$, and $R^5$ are hydrogen.

4. The lubricant base oil for power transmission according to claim 1, wherein n is 0 or 1; and R represents $C_{1-3}$ alkyl (preferably methyl).

5. The lubricant base oil for power transmission according to claim 1, wherein ring A is

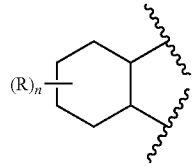

wherein R and n are as defined above.

6. The lubricant base oil for power transmission according to claim 1, wherein the content of the alicyclic dicarboxylic acid diester compound represented by general formula (1) in the lubricant base oil for power transmission is 70 wt % or more.

7. The lubricant base oil for power transmission according to claim 1, wherein the traction coefficient at 60° C. is 0.095 or more.

8. The lubricant base oil for power transmission according to claim 1, wherein the flash point is 210° C. or more.

9. The lubricant base oil for power transmission according to claim 1, wherein the pour point is 3° C. or less.

10. The lubricant base oil for power transmission according to claim 1, wherein the kinetic viscosity at 100° C. is 4 to 25 mm²/s.

11. The lubricant base oil for power transmission according to claim 1, wherein the lubricant base oil for power transmission is a lubricant base oil for traction drives.

12. A lubricant oil for power transmission comprising the lubricant base oil for power transmission according to claim 1.

13. An alicyclic dicarboxylic acid diester compound represented by general formula (1):

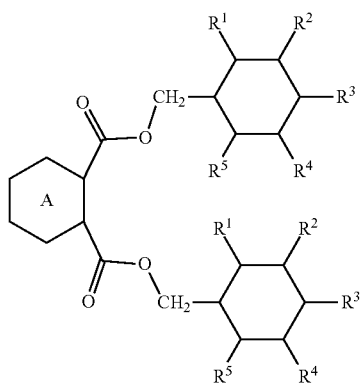

(1)

wherein $R^1$ to $R^5$ are the same or different, and each represents hydrogen or linear or branched $C_{1-4}$ alkyl, and two $R^1$, two $R^2$, two $R^3$, two $R^4$, and two $R^5$ may respectively be the same or different; and ring A is

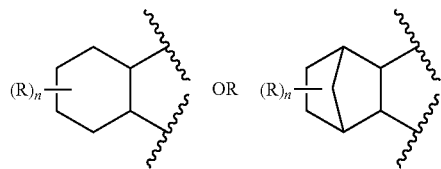

wherein R represents $C_{1-3}$ alkyl, and n represents 0, 1, or 2; when n represents 2, R may be the same or different.

14. The alicyclic dicarboxylic acid diester compound according to claim 13, wherein (a) R is $C_{1-3}$ alkyl (in particular, methyl) and n is 1 or 2; or (b) $R^3$ and/or $R^4$ is linear or branched $C_{1-4}$ alkyl (in particular, methyl).

15. A method for producing the alicyclic dicarboxylic acid diester compound represented by general formula (1) according to claim 13, comprising reacting a dicarboxylic acid represented by general formula (2),

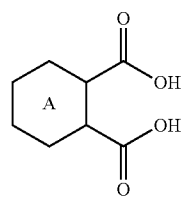

(2)

wherein ring A is

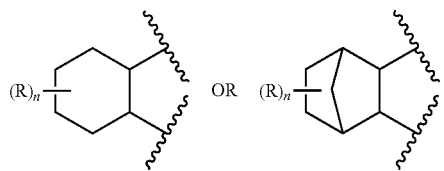

wherein R represents $C_{1-3}$ alkyl, and n represents 0, 1, or 2; when n represents 2, R may be the same or different, or an anhydride or dicarboxylic acid halide thereof with alcohol represented by general formula (3):

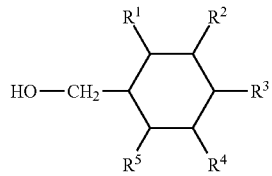

(3)

wherein $R^1$ to $R^5$ are the same or different, and each represents hydrogen or linear or branched $C_{1-4}$ alkyl.

* * * * *